US007588914B2

(12) United States Patent
Godzik et al.

(10) Patent No.: US 7,588,914 B2
(45) Date of Patent: Sep. 15, 2009

(54) BACTERIAL BCL-2 DOMAIN-CONTAINING POLYPEPTIDES, ENCODING NUCLEIC ACID MOLECULES, AND RELATED METHODS

(75) Inventors: Adam Godzik, San Diego, CA (US); John C. Reed, Rancho Santa Fe, CA (US)

(73) Assignee: Burnham Institute for Medical Research, La Jolla, CA (US)

( * ) Notice: Subject to any disclaimer, the term of this patent is extended or adjusted under 35 U.S.C. 154(b) by 594 days.

(21) Appl. No.: 10/294,445

(22) Filed: Nov. 13, 2002

(65) Prior Publication Data

US 2004/0023866 A1 Feb. 5, 2004

Related U.S. Application Data

(60) Provisional application No. 60/332,964, filed on Nov. 13, 2001.

(51) Int. Cl.
*C12N 15/00* (2006.01)

(52) U.S. Cl. .................. 435/69.1; 536/23.1; 536/24.32; 435/320.1; 435/325; 435/252.3; 435/254.2

(58) Field of Classification Search ....................... None
See application file for complete search history.

(56) References Cited

U.S. PATENT DOCUMENTS 6,294,328 B1 * 9/2001 Fleischmann et al. .......... 435/6

OTHER PUBLICATIONS

Philipp et al., (1996, Proc. Natl. Acad. Sci. USA, vol. 93, pp. 3132-3137).*

Verma et al. (Nature 1997, 389: 239-242).*

Adams and Cory, "Life-or-Death Decisions by the Bcl-2 Protein Family," *Trends Biochem. Sci*. 26(1):61-66 (2001).

Alouani, S., "Scintillation Proximity Binding Assay," *Methods Mol. Biol*. 138:135-141 (2000).

Bateman et al., "Pfam 3.1: 1313 Multiple Alignments and Profile HMMs Match the Majority of Proteins," *Nucleic Acids Res*. 27(1):260-262 (1999).

Bilbao et al., "Reduction of Ischemia-Reperfusion Injury of the Liver by In Vivo Adenovirus-Mediated gene Transfer of the Antipoptitic Bcl-2 Gene," *Annals of Surgery* 230(2):185-193 (1999).

Chen and Shapiro, "Affinity NMR," *Anal. Chem*. 71:669A-675A (1999).

Chittenden et al., "A Conserved Domain in Bak, Distinct from BH1 and BH2, Mediates Cell Death and Protein Binding Functions," *EMBO J*. 14(22):5589-5596 (1995).

Cosulich et al., "Regulation of apoptosis by BH3 domains in a cell-free system," *Curr. Biol*. 7(12):913-920 (1997).

Degterev et al., "Identification of small-molecule inhibitors of interaction between the BH3 domain and Bcl-$x_L$," *Nature Cell Biol*. 3:173-182 (2001).

Dunne et al., "Streptomyces Pneumonia in a Patient with Human Immunodeficiency Virus Infection: Case report and Review of the Literature on Invasive Streptomyces Infections," *Clin. Infec. Dis*. 27:93-96 (1998).

Elbashir et al., "Duplexes of 21-nucleotide RNAs mediate RNA interference in cultured mammalian cells," *Nature* 411(6836):494-498 (2001).

Everett et al., "The ability of herpes simple virus type 1 immediate-early protein Vmw110 to bind to a ubiquitin-specific protease contributes to its roles in the activation of gene expression and stimulation of virus replication," *J. Virol*. 73(1):417-426 (1999).

Fancy, D., "Elucidation of protein-protein interactions using chemical cross-linking or label transfer techniques," *Curr. Opin. Chem. Biol*. 4:28-33 (2000).

Galderisi et al., "Antisense oligonucleotides as therapeutic agents," *J. Cell. Physiol*. 181:251-257 (1999).

Hajduk et al., "High-throughput nuclear magnetic resonance-based screening," *J. Med. Chem*., 42:2315-2317 (1999).

Haraguchi et al., "Apoptotic protease activating factor 1 (Apaf-1) independent cell death suppression by Bcl-2," *J. Exp. Med*. 191(10):1709-1720 (2000).

Hengartner, M., "The biochemistry of apoptosis," *Nature* 407:770-776 (2000).

Hochman, A., "Programmed cell death in prokaryotes," *Crit. Rev. Micro*. 23(3):207-214 (1997).

Holinger et al., "Bak BH3 peptides antagonize Bcl-$x_L$ function and induce apoptosis through cytochrome *c*-independent activation of caspases," *J. Biol. Chem*. 274(19):13298-13304 (1999).

Igaki, "Drob-1, a *drosophila* member of the Bcl-2/CED-9 family that promotes cell death," *PNAS* 97(2):662-667 (2000).

Jen and Gewirtz, "Suppression of gene expression by targeted disruption of messenger RNA: Available options and current strategies," *Stem Cells* 18(5):307-319 (2000).

Leo et al., "Characterization of the antiapoptotic Bcl-2 family member myeloid cell leukemia-1 (Mcl-1) and the stimulation of its message by gonadotropins in the rat overy," *Enrocrinology* 140(12):5469-5477 (1999).

Lewin and Hauswirth, "Ribozyme gene therapy: applications for molecular medicine," *Trends Mol. Med*. 7(5):221-228 (2001).

Li et al., "Saturated BLAST: an automated multiple intermediate sequence search used to detect distant homology," *Bioinformatics* 16(12):1105-1110 (2000).

(Continued)

*Primary Examiner*—Misook Yu
(74) *Attorney, Agent, or Firm*—McDermott Will & Emery LLP

(57) ABSTRACT

The invention provides isolated Bcl-2 domain-containing polypeptides from Mycobacterial species, including *M. tuberculosis, M. avium, M. bovis, M. leprae* and *M. smegmatis,* and from Streptomyces species, including *S. coelicolor,* as well as modifications of such polypeptides, functional fragments therefrom, encoding nucleic acid molecules and specific antibodies. Also provided are methods for identifying polypeptides and compounds that associate with or modulate the activity of the Bcl-2 domain-containing polypeptides. Further provided are methods of modulating apoptosis and treating pathological conditions using the described nucleic acid molecules, polypeptides and compounds.

13 Claims, 2 Drawing Sheets

OTHER PUBLICATIONS

Maundrell et al., "Bcl-2 undergoes phosphorylation by c-Jun N-terminal kinase/stress-activated protein kinases in the presence of the constitutively active GTP-binding protein Rac1," *J. Biol. Chem.* 272(40):25238-25242 (1997).

McLafferty et al., "Techview: Biochemistry; Biomolecule mass spectrometry," *Science* 284:1289-1290 (1999).

Muchmore et al., "X-ray and NMR structure of human Bcl-$x_L$, an inhibitor of programmed cell death," *Nature* 381(6580):335-341 (1996).

Oberholzer et al., "Apoptosis in sepsis: a new target for therapeutic exploration," *FASEB J.* 15:879-892 (2001).

Petros et al., "Solution structure of the antiapoptotic protein bcl-2," *Proc. Natl. Acad. Sci.* 98(6):3012-3017 (2001).

Pratesi et al., "Role of Bcl-2 and its post-transcriptional modification in response to antitumor therapy," *Biochem. Pharm.* 61:381-386 (2001).

Reed, J. ed., "Apoptosis," *Meth. Enz.* vol. 322, Chapters 1-5, pp. 3-62, Chapters 15-17, pp. 177-201, Chapters 24-25, pp. 255-274 (2000) (Table of contents).

Rychlewski et al., "Comparison of sequence profiles. Strategies for structural predictions using sequence information," *Protein Sci.* 9:232-241 (2000).

Schmitz et al., "Regulation of death receptor-mediated apoptosis pathways," *Intern. J. Biochem. Cell Biol.* 32:1123-1136 (2000).

Shimizu et al., "BH4 domain of antiapoptotic Bcl-2 family members closes voltage-dependent anion channel and inhibits apoptotic mitochondrial changes and cell death," *Proc. Natl. Acad. Sci. USA* 97(7):3100-3105 (2000).

Shinnick and Good, "Mycobacterial taxonomy," *Eur. J. Clin. Microbiol. Infect. Dis.* 13(11):884-901 (1994).

Shuker et al., "Discovering high-affinity ligands for proteins: SAR by NMR," *Science* 274:1531-1534 (1996).

Srivastava et al., "Deletion of the loop region of Bcl-2 completely blocks paclitaxel-induced apoptosis," *Proc. Natl. Acad. Sci. USA* 96(7):3775-3780 (1999).

Su et al., "DNA damage and activated caspase-3 expression in neurons and astrocytes: evidence for apoptosis in frontotemporal dementia," *Exp. Neurol.* 163:9-19 (2000).

Tatusova and Madden, "BLAST 2 Sequences, a new tool for comparing protein and nucleotide sequences," *FEMS Microbiol. Lett.* 174:247-250 (1999).

Tschopp et al., "The fight of viruses against apoptosis," *Curr. Opin. Gene. Dev.* 8:82-87 (1998).

Wang et al., "Bcl-2 targets the protein kinase raf-1 to mitochondria," *Cell* 87:629-638 (1996).

Weinberger et al., "Recent trends in protein biochip technology," *Pharmacogenomics* 1(4):395-416 (2000).

Xu et al., "Assays for studying Bax-induced lethality in the yeast *Saccharomyces cerevisiae*," *Meth. Enz.* 332:283-296 (2000).

Xu and Reed, "Bax inhibitor-1, a mammalian apoptosis suppressor identified by functional screening in yeast," *Mol. Cell* 1:337-346 (1998).

Yamamura ed. et al., *Methods in Neurotransmitter Receptor Analysis*, Raven Press, New York (1990).

Genbank Accession No. AAB87418, (GI: 2645560).
Genbank Accession No. AAF39129, (GI: 7190300).
Genbank Accession No. AAG33252, (GI: 11245811).
Genbank Accession No. AAK47594, (GI: 13883066).
Genbank Accession No. AB018553, (GI: 6472616).
Genbank Accession No. AE001273.
Genbank Accession No. AE002160.
Genbank Accession No. AL021646, (GI: 3242278).
Genbank Accession No. AL035212, (GI: 4160309).
Genbank Accession No. AL123456.
Genbank Accession No. AL450380.
Genbank Accession No. BAA87062, (GI: 6472619).
Genbank Accession No. C64998, (GI: 7466311).
Genbank Accession No. CAA16631, (GI: 2827576).
Genbank Accession No. CAA22803, (GI: 4160332).
Genbank Accession No. D70947, (GI: 7477511).
Genbank Accession No. D71460, (GI: 7468961).
Genbank Accession No. NP_217682.
Genbank Accession No. P42485, (GI: 1169456).
Genbank Accession No. Q16548, (GI: 2493280).
Genbank Accession No. T35919, (GI: 7481597).
Genbank Accession No. 1GJHA, (GI: 14719780).
GNL: CBCUMN_1770 mycpara_contig2089.
GNL: pf12|Stanford_Chr12Contig05.001215.
GNL: Sanger_601|S.typhi_CT18.
GNL: Sanger_1765|mbovis_Contig264.
GNL: Sanger_1769 mleprae_Mycobacterium leprae.
GNL: TIGR|M.avium_243.
GNL: TIGR_1772|msmeg_2927.
GNL: TIGR_5691|T.brucei_32P4.TR M13 Trypansoma brucei.
GNL: TIGR_83354|cpsitt_148.
GNL: TIGR_1773|gmt3737.
GNL: WUGSC_32027|Spara_B_Spa.0.21909.
GNL: WUGSC_99287|Smlt2-Contig1457.

* cited by examiner

SEQUENCE LISTING

```
<160> NUMBER OF SEQ ID NOS: 30

<210> SEQ ID NO 1
<211> LENGTH: 960
<212> TYPE: DNA
<213> ORGANISM: Mycobacterium tuberculosis
<220> FEATURE:
<221> NAME/KEY: CDS
<222> LOCATION: (1)...(957)

<400> SEQUENCE: 1

atg ccc ggt act aag ccc ggt agt gac aaa ccg aca ggg cgc gtc gtc        48
Met Pro Gly Thr Lys Pro Gly Ser Asp Lys Pro Thr Gly Arg Val Val
1               5                   10                  15

gtc gtg atc gtg ctc ttg atg ctt gct ggc gct gcc ctg cgc ggc cac        96
Val Val Ile Val Leu Leu Met Leu Ala Gly Ala Ala Leu Arg Gly His
            20                  25                  30

ctg ccg gcc gac gac ggt gca ccg ctc gcg gcg gcc ggc ggc agc cgg       144
Leu Pro Ala Asp Asp Gly Ala Pro Leu Ala Ala Ala Gly Gly Ser Arg
        35                  40                  45

gcg gcg ctg atg ttc att gtc gcc gca ctt gcc gcg acg ctc gcg ctg       192
Ala Ala Leu Met Phe Ile Val Ala Ala Leu Ala Ala Thr Leu Ala Leu
    50                  55                  60

ata gcg ctc gcc atc atc acc cgg ttg cga cat ccg ctc ccg gtg gcg       240
Ile Ala Leu Ala Ile Ile Thr Arg Leu Arg His Pro Leu Pro Val Ala
65                  70                  75                  80

ccc agc gcg ggg gag ctc tcg gca atg ctt ggc ggt gca gca ggg cgt       288
Pro Ser Ala Gly Glu Leu Ser Ala Met Leu Gly Gly Ala Ala Gly Arg
                85                  90                  95

ccg aac tgg cgt gtg ctg ttg ctc gga ctc ggg aca atc ctg gcc tgg       336
Pro Asn Trp Arg Val Leu Leu Leu Gly Leu Gly Thr Ile Leu Ala Trp
            100                 105                 110

ctg ctg att gcg ata ctg ctg gca cgg ttg ttc gtg ccc gat gat gtc       384
Leu Leu Ile Ala Ile Leu Leu Ala Arg Leu Phe Val Pro Asp Asp Val
        115                 120                 125

ggt cct gct gcg ccc ata ccg gat tca acc gct acg ccg gat gct tcc       432
Gly Pro Ala Ala Pro Ile Pro Asp Ser Thr Ala Thr Pro Asp Ala Ser
    130                 135                 140

agc acc acg ccg tcg cgc ccg caa ccg ccg caa gac aac aat gac gac       480
Ser Thr Thr Pro Ser Arg Pro Gln Pro Pro Gln Asp Asn Asn Asp Asp
145                 150                 155                 160

gtg ctc ggc att ctc ttt gcc agc aca atc ggc ctg ttc ttg atg gtc       528
Val Leu Gly Ile Leu Phe Ala Ser Thr Ile Gly Leu Phe Leu Met Val
                165                 170                 175

gtc gcg ggg tcg ctg att acc tcg cga cga cag cgc aag tcg gca ccg       576
Val Ala Gly Ser Leu Ile Thr Ser Arg Arg Gln Arg Lys Ser Ala Pro
            180                 185                 190

gct cgt atc agt ggc gat cgc atc gag tct ccg gcg ccc tcg gcg cgt       624
Ala Arg Ile Ser Gly Asp Arg Ile Glu Ser Pro Ala Pro Ser Ala Arg
        195                 200                 205

tcg gaa tca ctg gcg cgt gcc gcc gag atc gga ctg gcc gag atg gcc       672
Ser Glu Ser Leu Ala Arg Ala Ala Glu Ile Gly Leu Ala Glu Met Ala
    210                 215                 220

gac ctc cgc cgc gaa cca cgg gag gcg ata att gcg tgt tac gtg gcg       720
Asp Leu Arg Arg Glu Pro Arg Glu Ala Ile Ile Ala Cys Tyr Val Ala
225                 230                 235                 240

atg gag cgt gaa ctg tcg cat gtt ccc ggt gtt gcc cct cag gac ttc       768
Met Glu Arg Glu Leu Ser His Val Pro Gly Val Ala Pro Gln Asp Phe
                245                 250                 255
```

-continued

```
gac acc ccg acc gag gtg ctg gcc cga gcc gtc gaa cac cgt gcg ctc      816
Asp Thr Pro Thr Glu Val Leu Ala Arg Ala Val Glu His Arg Ala Leu
            260                 265                 270

cat ggt gct agt gcc gcc gcg ttg gtg agc ctg ttc gcc gag gcg cgt      864
His Gly Ala Ser Ala Ala Ala Leu Val Ser Leu Phe Ala Glu Ala Arg
        275                 280                 285

ttt agc ccg cac gtg atg aac gag gag cac cgt gag gtg gcg atg cgt      912
Phe Ser Pro His Val Met Asn Glu Glu His Arg Glu Val Ala Met Arg
    290                 295                 300

ttg ctt cga ctg gtt ctt gac gaa ctg agc act cgg acc gct ata          957
Leu Leu Arg Leu Val Leu Asp Glu Leu Ser Thr Arg Thr Ala Ile
305                 310                 315

tga                                                                  960


<210> SEQ ID NO 2
<211> LENGTH: 319
<212> TYPE: PRT
<213> ORGANISM: Mycobacterium tuberculosis

<400> SEQUENCE: 2

Met Pro Gly Thr Lys Pro Gly Ser Asp Lys Pro Thr Gly Arg Val Val
1               5                   10                  15

Val Val Ile Val Leu Leu Met Leu Ala Gly Ala Ala Leu Arg Gly His
            20                  25                  30

Leu Pro Ala Asp Asp Gly Ala Pro Leu Ala Ala Ala Gly Gly Ser Arg
        35                  40                  45

Ala Ala Leu Met Phe Ile Val Ala Ala Leu Ala Ala Thr Leu Ala Leu
    50                  55                  60

Ile Ala Leu Ala Ile Ile Thr Arg Leu Arg His Pro Leu Pro Val Ala
65                  70                  75                  80

Pro Ser Ala Gly Glu Leu Ser Ala Met Leu Gly Gly Ala Ala Gly Arg
                85                  90                  95

Pro Asn Trp Arg Val Leu Leu Leu Gly Leu Gly Thr Ile Leu Ala Trp
            100                 105                 110

Leu Leu Ile Ala Ile Leu Leu Ala Arg Leu Phe Val Pro Asp Asp Val
        115                 120                 125

Gly Pro Ala Ala Pro Ile Pro Asp Ser Thr Ala Thr Pro Asp Ala Ser
    130                 135                 140

Ser Thr Thr Pro Ser Arg Pro Gln Pro Pro Gln Asp Asn Asn Asp Asp
145                 150                 155                 160

Val Leu Gly Ile Leu Phe Ala Ser Thr Ile Gly Leu Phe Leu Met Val
                165                 170                 175

Val Ala Gly Ser Leu Ile Thr Ser Arg Arg Gln Arg Lys Ser Ala Pro
            180                 185                 190

Ala Arg Ile Ser Gly Asp Arg Ile Glu Ser Pro Ala Pro Ser Ala Arg
        195                 200                 205

Ser Glu Ser Leu Ala Arg Ala Ala Glu Ile Gly Leu Ala Glu Met Ala
    210                 215                 220

Asp Leu Arg Arg Glu Pro Arg Glu Ala Ile Ile Ala Cys Tyr Val Ala
225                 230                 235                 240

Met Glu Arg Glu Leu Ser His Val Pro Gly Val Ala Pro Gln Asp Phe
                245                 250                 255

Asp Thr Pro Thr Glu Val Leu Ala Arg Ala Val Glu His Arg Ala Leu
            260                 265                 270

His Gly Ala Ser Ala Ala Ala Leu Val Ser Leu Phe Ala Glu Ala Arg
        275                 280                 285
```

-continued

```
Phe Ser Pro His Val Met Asn Glu Glu His Arg Glu Val Ala Met Arg
    290                 295                 300

Leu Leu Arg Leu Val Leu Asp Glu Leu Ser Thr Arg Thr Ala Ile
305                 310                 315


<210> SEQ ID NO 3
<211> LENGTH: 321
<212> TYPE: PRT
<213> ORGANISM: Mycobacterium tuberculosis

<400> SEQUENCE: 3

Met Arg Met Pro Gly Thr Lys Pro Gly Ser Asp Lys Pro Thr Gly Arg
1               5                   10                  15

Val Val Val Val Ile Val Leu Leu Met Leu Ala Gly Ala Ala Leu Arg
            20                  25                  30

Gly His Leu Pro Ala Asp Asp Gly Ala Pro Leu Ala Ala Ala Gly Gly
        35                  40                  45

Ser Arg Ala Ala Leu Met Phe Ile Val Ala Ala Leu Ala Ala Thr Leu
    50                  55                  60

Ala Leu Ile Ala Leu Ala Ile Ile Thr Arg Leu Arg His Pro Leu Pro
65                  70                  75                  80

Val Ala Pro Ser Ala Gly Glu Leu Ser Ala Met Leu Gly Gly Ala Ala
                85                  90                  95

Gly Arg Pro Asn Trp Arg Val Leu Leu Leu Gly Leu Gly Thr Ile Leu
            100                 105                 110

Ala Trp Leu Leu Ile Ala Ile Leu Leu Ala Arg Leu Phe Val Pro Asp
        115                 120                 125

Asp Val Gly Pro Ala Ala Pro Ile Pro Asp Ser Thr Ala Thr Pro Asp
    130                 135                 140

Ala Ser Ser Thr Thr Pro Ser Arg Pro Gln Pro Pro Gln Asp Asn Asn
145                 150                 155                 160

Asp Asp Val Leu Gly Ile Leu Phe Ala Ser Thr Ile Gly Leu Phe Leu
                165                 170                 175

Met Val Val Ala Gly Ser Leu Ile Thr Ser Arg Arg Gln Arg Lys Ser
            180                 185                 190

Ala Pro Ala Arg Ile Ser Gly Asp Arg Ile Glu Ser Pro Ala Pro Ser
        195                 200                 205

Ala Arg Ser Glu Ser Leu Ala Arg Ala Ala Glu Ile Gly Leu Ala Glu
    210                 215                 220

Met Ala Asp Leu Arg Arg Glu Pro Arg Glu Ala Ile Ile Ala Cys Tyr
225                 230                 235                 240

Val Ala Met Glu Arg Glu Leu Ser His Val Pro Gly Val Ala Pro Gln
                245                 250                 255

Asp Phe Asp Thr Pro Thr Glu Val Leu Ala Arg Ala Val Glu His Arg
            260                 265                 270

Ala Leu His Gly Ala Ser Ala Ala Ala Leu Val Ser Leu Phe Ala Glu
        275                 280                 285

Ala Arg Phe Ser Pro His Val Met Asn Glu Glu His Arg Glu Val Ala
    290                 295                 300

Met Arg Leu Leu Arg Leu Val Leu Asp Glu Leu Ser Thr Arg Thr Ala
305                 310                 315                 320

Ile


<210> SEQ ID NO 4
```

-continued

```
<211> LENGTH: 379
<212> TYPE: DNA
<213> ORGANISM: Mycobacterium tuberculosis
<220> FEATURE:
<221> NAME/KEY: CDS
<222> LOCATION: (2)...(379)

<400> SEQUENCE: 4

g cgc aag tcg gca ccg gct cgt atc agt ggc gat cgc atc gag tct ccg      49
  Arg Lys Ser Ala Pro Ala Arg Ile Ser Gly Asp Arg Ile Glu Ser Pro
  1               5                   10                  15

gcg ccc tcg gcg cgt tcg gaa tca ctg gcg cgt gcc gcc gag atc gga       97
Ala Pro Ser Ala Arg Ser Glu Ser Leu Ala Arg Ala Ala Glu Ile Gly
            20                  25                  30

ctg gcc gag atg gcc gac ctc cgc cgc gaa cca cgg gag gcg ata att      145
Leu Ala Glu Met Ala Asp Leu Arg Arg Glu Pro Arg Glu Ala Ile Ile
        35                  40                  45

gcg tgt tac gtg gcg atg gag cgt gaa ctg tcg cat gtt ccc ggt gtt      193
Ala Cys Tyr Val Ala Met Glu Arg Glu Leu Ser His Val Pro Gly Val
    50                  55                  60

gcc cct cag gac ttc gac acc ccg acc gag gtg ctg gcc cga gcc gtc      241
Ala Pro Gln Asp Phe Asp Thr Pro Thr Glu Val Leu Ala Arg Ala Val
65                  70                  75                  80

gaa cac cgt gcg ctc cat ggt gct agt gcc gcc gcg ttg gtg agc ctg      289
Glu His Arg Ala Leu His Gly Ala Ser Ala Ala Ala Leu Val Ser Leu
                85                  90                  95

ttc gcc gag gcg cgt ttt agc ccg cac gtg atg aac gag gag cac cgt      337
Phe Ala Glu Ala Arg Phe Ser Pro His Val Met Asn Glu Glu His Arg
            100                 105                 110

gag gtg gcg atg cgt ttg ctt cga ctg gtt ctt gac gaa ctg              379
Glu Val Ala Met Arg Leu Leu Arg Leu Val Leu Asp Glu Leu
        115                 120                 125


<210> SEQ ID NO 5
<211> LENGTH: 126
<212> TYPE: PRT
<213> ORGANISM: Mycobacterium tuberculosis

<400> SEQUENCE: 5

Arg Lys Ser Ala Pro Ala Arg Ile Ser Gly Asp Arg Ile Glu Ser Pro
1               5                   10                  15

Ala Pro Ser Ala Arg Ser Glu Ser Leu Ala Arg Ala Ala Glu Ile Gly
            20                  25                  30

Leu Ala Glu Met Ala Asp Leu Arg Arg Glu Pro Arg Glu Ala Ile Ile
        35                  40                  45

Ala Cys Tyr Val Ala Met Glu Arg Glu Leu Ser His Val Pro Gly Val
    50                  55                  60

Ala Pro Gln Asp Phe Asp Thr Pro Thr Glu Val Leu Ala Arg Ala Val
65                  70                  75                  80

Glu His Arg Ala Leu His Gly Ala Ser Ala Ala Ala Leu Val Ser Leu
                85                  90                  95

Phe Ala Glu Ala Arg Phe Ser Pro His Val Met Asn Glu Glu His Arg
            100                 105                 110

Glu Val Ala Met Arg Leu Leu Arg Leu Val Leu Asp Glu Leu
        115                 120                 125


<210> SEQ ID NO 6
<211> LENGTH: 1266
<212> TYPE: DNA
<213> ORGANISM: Mycobacterium avium
<220> FEATURE:
```

-continued

<221> NAME/KEY: CDS
<222> LOCATION: (1)...(1263)

<400> SEQUENCE: 6

```
atg agc aaa gcc agt gcc gca cca gcg gca ggc aac cgg tcg agt ggt       48
Met Ser Lys Ala Ser Ala Ala Pro Ala Ala Gly Asn Arg Ser Ser Gly
1               5                   10                  15

gtg ccg atg ccc ggg atg gac aag ccg acg ggg cgg gtc gtc gcc ctg       96
Val Pro Met Pro Gly Met Asp Lys Pro Thr Gly Arg Val Val Ala Leu
            20                  25                  30

atc gtt ctg ttg ctc gtg gtc gcc gcc gcc ctg cgc ggg tac ctg ccc      144
Ile Val Leu Leu Leu Val Val Ala Ala Ala Leu Arg Gly Tyr Leu Pro
        35                  40                  45

gcc caa cac gac gcg acg cgc agc gag gcg ggc ggc cgg gcg gcg ctg      192
Ala Gln His Asp Ala Thr Arg Ser Glu Ala Gly Gly Arg Ala Ala Leu
    50                  55                  60

ggc ctg gtg gtg gcc atc ctc gcg gtg acg ctg gcg ctg atc gcg gtc      240
Gly Leu Val Val Ala Ile Leu Ala Val Thr Leu Ala Leu Ile Ala Val
65                  70                  75                  80

gcg atc gtc gcg cgg ttg aag gac ccg cgg gcg ccg gcc ccg ccc gcc      288
Ala Ile Val Ala Arg Leu Lys Asp Pro Arg Ala Pro Ala Pro Pro Ala
                85                  90                  95

ggc gcg ctg tcg gag acg ctg ggc gcc ggc agg ggc cgc ccg acc tgg      336
Gly Ala Leu Ser Glu Thr Leu Gly Ala Gly Arg Gly Arg Pro Thr Trp
            100                 105                 110

cgg gtc gtc gcc ctg atc gtt ctg ttg ctc gtg gtc gcc gcc gcc ctg      384
Arg Val Val Ala Leu Ile Val Leu Leu Leu Val Val Ala Ala Ala Leu
        115                 120                 125

cgc ggg tac ctg ccc gcc caa cac gac gcg acg cgc agc gag gcg ggc      432
Arg Gly Tyr Leu Pro Ala Gln His Asp Ala Thr Arg Ser Glu Ala Gly
    130                 135                 140

ggc cgg gcg gcg ctg ggc ctg gtg gtg gcc atc ctc gcg gtg acg ctg      480
Gly Arg Ala Ala Leu Gly Leu Val Val Ala Ile Leu Ala Val Thr Leu
145                 150                 155                 160

gcg ctg atc gcg gtc gcg atc gtc gcg cgg ttg aag gac ccg cgg gcg      528
Ala Leu Ile Ala Val Ala Ile Val Ala Arg Leu Lys Asp Pro Arg Ala
                165                 170                 175

ccg gcc ccg ccc gcc ggc gcg ctg tcg gag acg ctg ggc gcc ggc agg      576
Pro Ala Pro Pro Ala Gly Ala Leu Ser Glu Thr Leu Gly Ala Gly Arg
            180                 185                 190

ggc cgc ccg acc tgg cgg gtg ttg ctg atc ggg ctc ggc gtg atc gtg      624
Gly Arg Pro Thr Trp Arg Val Leu Leu Ile Gly Leu Gly Val Ile Val
        195                 200                 205

gcc tgg ctg ctg atc gtg atg ctg ttg gcc cgg ctg ttc gcg tcg cac      672
Ala Trp Leu Leu Ile Val Met Leu Leu Ala Arg Leu Phe Ala Ser His
    210                 215                 220

ggg ctc gcg ccc gcc ccg ccg ccc ggc acc ggt gcg tcg ccg cca ccg      720
Gly Leu Ala Pro Ala Pro Pro Pro Gly Thr Gly Ala Ser Pro Pro Pro
225                 230                 235                 240

cac ccg gcg gca ccc ccg gca ccg ccg ccg cag cac ccg cag cgt ccg      768
His Pro Ala Ala Pro Pro Ala Pro Pro Pro Gln His Pro Gln Arg Pro
                245                 250                 255

cgc gac ggg tcg cag gac acg ctg ggc atc ctg ctc gcc ggc acc gtc      816
Arg Asp Gly Ser Gln Asp Thr Leu Gly Ile Leu Leu Ala Gly Thr Val
            260                 265                 270

gcg atg ctg ttg atg gtc gtc gcc tca gcg gtg gcc ggc gcg cgg cgc      864
Ala Met Leu Leu Met Val Val Ala Ser Ala Val Ala Gly Ala Arg Arg
        275                 280                 285

cgg tgg cgg tcg ccg gca ccg gct gtc ccc gac gaa ccg gcc gaa aac      912
Arg Trp Arg Ser Pro Ala Pro Ala Val Pro Asp Glu Pro Ala Glu Asn
```

-continued

```
    290                 295                 300

ccg gcg ccg caa cca cat tcg gag tcg ctg gcg cgt gcg gcc gaa cgc      960
Pro Ala Pro Gln Pro His Ser Glu Ser Leu Ala Arg Ala Ala Glu Arg
305                 310                 315                 320

ggg ttg gcc gag atg gcc gac ctg cgc cgc gac ccc cgc gag gcc atc     1008
Gly Leu Ala Glu Met Ala Asp Leu Arg Arg Asp Pro Arg Glu Ala Ile
                325                 330                 335

atc gcc tgc tac gcc gcg atg gaa cgc gaa ctg gcg cac gtt ccc ggt     1056
Ile Ala Cys Tyr Ala Ala Met Glu Arg Glu Leu Ala His Val Pro Gly
            340                 345                 350

gcc gtg ccg cag gac ttc gac acc ccc agc gag gtg ctg gcc cgc gcg     1104
Ala Val Pro Gln Asp Phe Asp Thr Pro Ser Glu Val Leu Ala Arg Ala
        355                 360                 365

gtg gaa cac cat gcg ctg cac gcc gac aac gcc gtc cag ctg gtg aac     1152
Val Glu His His Ala Leu His Ala Asp Asn Ala Val Gln Leu Val Asn
    370                 375                 380

ctg ttc acc gag gcg cgg ttc agc ccg cac gtg atg aac gag ggc cac     1200
Leu Phe Thr Glu Ala Arg Phe Ser Pro His Val Met Asn Glu Gly His
385                 390                 395                 400

cgc gac gtg gcg gtg cgg gtg ttg cgg ctg gtg ctc gac gaa ctg ggg     1248
Arg Asp Val Ala Val Arg Val Leu Arg Leu Val Leu Asp Glu Leu Gly
                405                 410                 415

agc cgg agt gtc gca tga                                             1266
Ser Arg Ser Val Ala
            420


<210> SEQ ID NO 7
<211> LENGTH: 421
<212> TYPE: PRT
<213> ORGANISM: Mycobacterium avium

<400> SEQUENCE: 7

Met Ser Lys Ala Ser Ala Ala Pro Ala Ala Gly Asn Arg Ser Ser Gly
1               5                   10                  15

Val Pro Met Pro Gly Met Asp Lys Pro Thr Gly Arg Val Val Ala Leu
            20                  25                  30

Ile Val Leu Leu Leu Val Val Ala Ala Ala Leu Arg Gly Tyr Leu Pro
        35                  40                  45

Ala Gln His Asp Ala Thr Arg Ser Glu Ala Gly Gly Arg Ala Ala Leu
    50                  55                  60

Gly Leu Val Val Ala Ile Leu Ala Val Thr Leu Ala Leu Ile Ala Val
65                  70                  75                  80

Ala Ile Val Ala Arg Leu Lys Asp Pro Arg Ala Pro Ala Pro Pro Ala
                85                  90                  95

Gly Ala Leu Ser Glu Thr Leu Gly Ala Gly Arg Gly Arg Pro Thr Trp
            100                 105                 110

Arg Val Val Ala Leu Ile Val Leu Leu Leu Val Val Ala Ala Ala Leu
        115                 120                 125

Arg Gly Tyr Leu Pro Ala Gln His Asp Ala Thr Arg Ser Glu Ala Gly
    130                 135                 140

Gly Arg Ala Ala Leu Gly Leu Val Val Ala Ile Leu Ala Val Thr Leu
145                 150                 155                 160

Ala Leu Ile Ala Val Ala Ile Val Ala Arg Leu Lys Asp Pro Arg Ala
                165                 170                 175

Pro Ala Pro Pro Ala Gly Ala Leu Ser Glu Thr Leu Gly Ala Gly Arg
            180                 185                 190

Gly Arg Pro Thr Trp Arg Val Leu Leu Ile Gly Leu Gly Val Ile Val
```

-continued 195 200 205

Ala Trp Leu Leu Ile Val Met Leu Leu Ala Arg Leu Phe Ala Ser His
210 215 220

Gly Leu Ala Pro Ala Pro Pro Pro Gly Thr Gly Ala Ser Pro Pro Pro
225 230 235 240

His Pro Ala Ala Pro Pro Ala Pro Pro Pro Gln His Pro Gln Arg Pro
245 250 255

Arg Asp Gly Ser Gln Asp Thr Leu Gly Ile Leu Leu Ala Gly Thr Val
260 265 270

Ala Met Leu Leu Met Val Val Ala Ser Ala Val Ala Gly Ala Arg Arg
275 280 285

Arg Trp Arg Ser Pro Ala Pro Ala Val Pro Asp Glu Pro Ala Glu Asn
290 295 300

Pro Ala Pro Gln Pro His Ser Glu Ser Leu Ala Arg Ala Ala Glu Arg
305 310 315 320

Gly Leu Ala Glu Met Ala Asp Leu Arg Arg Asp Pro Arg Glu Ala Ile
325 330 335

Ile Ala Cys Tyr Ala Ala Met Glu Arg Glu Leu Ala His Val Pro Gly
340 345 350

Ala Val Pro Gln Asp Phe Asp Thr Pro Ser Glu Val Leu Ala Arg Ala
355 360 365

Val Glu His His Ala Leu His Ala Asp Asn Ala Val Gln Leu Val Asn
370 375 380

Leu Phe Thr Glu Ala Arg Phe Ser Pro His Val Met Asn Glu Gly His
385 390 395 400

Arg Asp Val Ala Val Arg Val Leu Arg Leu Val Leu Asp Glu Leu Gly
405 410 415

Ser Arg Ser Val Ala
420

<210> SEQ ID NO 8
<211> LENGTH: 378
<212> TYPE: DNA
<213> ORGANISM: Mycobacterium avium
<220> FEATURE:
<221> NAME/KEY: CDS
<222> LOCATION: (1)...(378)

<400> SEQUENCE: 8 tgg cgg tcg ccg gca ccg gct gtc ccc gac gaa ccg gcc gaa aac ccg 48
Trp Arg Ser Pro Ala Pro Ala Val Pro Asp Glu Pro Ala Glu Asn Pro
1 5 10 15 gcg ccg caa cca cat tcg gag tcg ctg gcg cgt gcg gcc gaa cgc ggg 96
Ala Pro Gln Pro His Ser Glu Ser Leu Ala Arg Ala Ala Glu Arg Gly
20 25 30 ttg gcc gag atg gcc gac ctg cgc cgc gac ccc cgc gag gcc atc atc 144
Leu Ala Glu Met Ala Asp Leu Arg Arg Asp Pro Arg Glu Ala Ile Ile
35 40 45 gcc tgc tac gcc gcg atg gaa cgc gaa ctg gcg cac gtt ccc ggt gcc 192
Ala Cys Tyr Ala Ala Met Glu Arg Glu Leu Ala His Val Pro Gly Ala
50 55 60 gtg ccg cag gac ttc gac acc ccc agc gag gtg ctg gcc cgc gcg gtg 240
Val Pro Gln Asp Phe Asp Thr Pro Ser Glu Val Leu Ala Arg Ala Val
65 70 75 80 gaa cac cat gcg ctg cac gcc gac aac gcc gtc cag ctg gtg aac ctg 288
Glu His His Ala Leu His Ala Asp Asn Ala Val Gln Leu Val Asn Leu
85 90 95

-continued

```
ttc acc gag gcg cgg ttc agc ccg cac gtg atg aac gag ggc cac cgc      336
Phe Thr Glu Ala Arg Phe Ser Pro His Val Met Asn Glu Gly His Arg
            100                 105                 110

gac gtg gcg gtg cgg gtg ttg cgg ctg gtg ctc gac gaa ctg              378
Asp Val Ala Val Arg Val Leu Arg Leu Val Leu Asp Glu Leu
        115                 120                 125


<210> SEQ ID NO 9
<211> LENGTH: 126
<212> TYPE: PRT
<213> ORGANISM: Mycobacterium avium

<400> SEQUENCE: 9

Trp Arg Ser Pro Ala Pro Ala Val Pro Asp Glu Pro Ala Glu Asn Pro
1               5                   10                  15

Ala Pro Gln Pro His Ser Glu Ser Leu Ala Arg Ala Ala Glu Arg Gly
            20                  25                  30

Leu Ala Glu Met Ala Asp Leu Arg Arg Asp Pro Arg Glu Ala Ile Ile
        35                  40                  45

Ala Cys Tyr Ala Ala Met Glu Arg Glu Leu Ala His Val Pro Gly Ala
    50                  55                  60

Val Pro Gln Asp Phe Asp Thr Pro Ser Glu Val Leu Ala Arg Ala Val
65                  70                  75                  80

Glu His His Ala Leu His Ala Asp Asn Ala Val Gln Leu Val Asn Leu
                85                  90                  95

Phe Thr Glu Ala Arg Phe Ser Pro His Val Met Asn Glu Gly His Arg
            100                 105                 110

Asp Val Ala Val Arg Val Leu Arg Leu Val Leu Asp Glu Leu
        115                 120                 125


<210> SEQ ID NO 10
<211> LENGTH: 769
<212> TYPE: DNA
<213> ORGANISM: Mycobacterium leprae
<220> FEATURE:
<221> NAME/KEY: CDS
<222> LOCATION: (1)...(769)
<220> FEATURE:
<221> NAME/KEY: misc_feature
<222> LOCATION: 333
<223> OTHER INFORMATION: n = A,T,C or G

<400> SEQUENCE: 10

atg gtc gcg ctg tat ggt gat cgt gta gtt gcg gaa acc ctc gct ttg       48
Met Val Ala Leu Tyr Gly Asp Arg Val Val Ala Glu Thr Leu Ala Leu
1               5                   10                  15

gca acc agg gct ggg gag ctg tcc gat atc gat atg cat gga ggt ggg       96
Ala Thr Arg Ala Gly Glu Leu Ser Asp Ile Asp Met His Gly Gly Gly
            20                  25                  30
acg aca aga ccg acc tgg agc gtg tta ctg aac gga ctc gcg gtg atc      144
Thr Thr Arg Pro Thr Trp Ser Val Leu Leu Asn Gly Leu Ala Val Ile
        35                  40                  45

gtg gcc tgg ttg ctg atc gtg ata ttg ctg gcc tgg tta ttc gcg cca      192
Val Ala Trp Leu Leu Ile Val Ile Leu Leu Ala Trp Leu Phe Ala Pro
    50                  55                  60

cac aac gtc aat ccc tcg gct tct ata acg gat tcg agt gta ccg ctg      240
His Asn Val Asn Pro Ser Ala Ser Ile Thr Asp Ser Ser Val Pro Leu
65                  70                  75                  80

gtg gtg cag gat acc gaa acg cca ccg aag cag ctt caa cac gat acc      288
Val Val Gln Asp Thr Glu Thr Pro Pro Lys Gln Leu Gln His Asp Thr
                85                  90                  95

ggg gac atg gtg gga atc ctt cgt gca agc gcg gta cca atg ttn ttg      336
```

-continued

Gly Asp Met Val Gly Ile Leu Arg Ala Ser Ala Val Pro Met Xaa Leu
100 105 110 att gtt gtc gcg ggt gcg gtt atc ggg ccg cga cgg cgg tgg cgc gcg 384
Ile Val Val Ala Gly Ala Val Ile Gly Pro Arg Arg Arg Trp Arg Ala
115 120 125 gct cag ata cca cgg ccg gtc ttc ctc act gac gat aac gtc gca tcc 432
Ala Gln Ile Pro Arg Pro Val Phe Leu Thr Asp Asp Asn Val Ala Ser
130 135 140 gta aca ctc acg aag cat tcg gaa tta ttg ttg cga gca gcc gaa ttc 480
Val Thr Leu Thr Lys His Ser Glu Leu Leu Leu Arg Ala Ala Glu Phe
145 150 155 160 ggc ttg gcc tag atg tag gac ctc acg tga gaa cca cga gag gcg atc 528
Gly Leu Ala * Met * Asp Leu Thr * Glu Pro Arg Glu Ala Ile
165 170 aac gtc tgt tac gtg gag atg gaa cgt gaa ctt gcg cat gtt ctc gga 576
Asn Val Cys Tyr Val Glu Met Glu Arg Glu Leu Ala His Val Leu Gly
175 180 185 gat gtt ccc cag gaa tgc ggc acc ttg acc tag gaa ttc gat cga aaa 624
Asp Val Pro Gln Glu Cys Gly Thr Leu Thr * Glu Phe Asp Arg Lys
190 195 200 gtg gat cat cat gcg ctg cat gat gat aac act gtc cag ttg gcg aac 672
Val Asp His His Ala Leu His Asp Asp Asn Thr Val Gln Leu Ala Asn
205 210 215 220 ctg ttc gaa gaa aca cgg ttt atc tag cat gtt atg aat gag cga cat 720
Leu Phe Glu Glu Thr Arg Phe Ile * His Val Met Asn Glu Arg His
225 230 235 agt gag ata gcg gtc taa gtg ctg ctg ata gtt ttt gtt gag ctt cgg 768
Ser Glu Ile Ala Val * Val Leu Leu Ile Val Phe Val Glu Leu Arg
240 245 250 c 769

<210> SEQ ID NO 11
<211> LENGTH: 250
<212> TYPE: PRT
<213> ORGANISM: Mycobacterium leprae
<220> FEATURE:
<221> NAME/KEY: VARIANT
<222> LOCATION: 111
<223> OTHER INFORMATION: Xaa = Any Amino Acid

<400> SEQUENCE: 11

Met Val Ala Leu Tyr Gly Asp Arg Val Val Ala Glu Thr Leu Ala Leu
1 5 10 15

Ala Thr Arg Ala Gly Glu Leu Ser Asp Ile Asp Met His Gly Gly Gly
20 25 30

Thr Thr Arg Pro Thr Trp Ser Val Leu Leu Asn Gly Leu Ala Val Ile
35 40 45

Val Ala Trp Leu Leu Ile Val Ile Leu Leu Ala Trp Leu Phe Ala Pro
50 55 60

His Asn Val Asn Pro Ser Ala Ser Ile Thr Asp Ser Ser Val Pro Leu
65 70 75 80

Val Val Gln Asp Thr Glu Thr Pro Pro Lys Gln Leu Gln His Asp Thr
85 90 95

Gly Asp Met Val Gly Ile Leu Arg Ala Ser Ala Val Pro Met Xaa Leu
100 105 110

Ile Val Val Ala Gly Ala Val Ile Gly Pro Arg Arg Arg Trp Arg Ala
115 120 125

Ala Gln Ile Pro Arg Pro Val Phe Leu Thr Asp Asp Asn Val Ala Ser
130 135 140

-continued

```
Val Thr Leu Thr Lys His Ser Glu Leu Leu Leu Arg Ala Ala Glu Phe
145                 150                 155                 160

Gly Leu Ala Met Asp Leu Thr Glu Pro Arg Glu Ala Ile Asn Val Cys
                165                 170                 175

Tyr Val Glu Met Glu Arg Glu Leu Ala His Val Leu Gly Asp Val Pro
            180                 185                 190

Gln Glu Cys Gly Thr Leu Thr Glu Phe Asp Arg Lys Val Asp His His
        195                 200                 205

Ala Leu His Asp Asp Asn Thr Val Gln Leu Ala Asn Leu Phe Glu Glu
    210                 215                 220

Thr Arg Phe Ile His Val Met Asn Glu Arg His Ser Glu Ile Ala Val
225                 230                 235                 240

Val Leu Leu Ile Val Phe Val Glu Leu Arg
                245                 250


<210> SEQ ID NO 12
<211> LENGTH: 390
<212> TYPE: DNA
<213> ORGANISM: Mycobacterium leprae
<220> FEATURE:
<221> NAME/KEY: CDS
<222> LOCATION: (1)...(390)

<400> SEQUENCE: 12

tgg cgc gcg gct cag ata cca cgg ccg gtc ttc ctc act gac gat aac       48
Trp Arg Ala Ala Gln Ile Pro Arg Pro Val Phe Leu Thr Asp Asp Asn
1               5                   10                  15

gtc gca tcc gta aca ctc acg aag cat tcg gaa tta ttg ttg cga gca       96
Val Ala Ser Val Thr Leu Thr Lys His Ser Glu Leu Leu Leu Arg Ala
            20                  25                  30

gcc gaa ttc ggc ttg gcc tag atg tag gac ctc acg tga gaa cca cga      144
Ala Glu Phe Gly Leu Ala  *  Met  *  Asp Leu Thr  *  Glu Pro Arg
        35                          40                      45

gag gcg atc aac gtc tgt tac gtg gag atg gaa cgt gaa ctt gcg cat      192
Glu Ala Ile Asn Val Cys Tyr Val Glu Met Glu Arg Glu Leu Ala His
                50                  55                  60

gtt ctc gga gat gtt ccc cag gaa tgc ggc acc ttg acc tag gaa ttc      240
Val Leu Gly Asp Val Pro Gln Glu Cys Gly Thr Leu Thr  *  Glu Phe
            65                  70                      75

gat cga aaa gtg gat cat cat gcg ctg cat gat gat aac act gtc cag      288
Asp Arg Lys Val Asp His His Ala Leu His Asp Asp Asn Thr Val Gln
            80                  85                  90

ttg gcg aac ctg ttc gaa gaa aca cgg ttt atc tag cat gtt atg aat      336
Leu Ala Asn Leu Phe Glu Glu Thr Arg Phe Ile  *  His Val Met Asn
        95                  100                 105

gag cga cat agt gag ata gcg gtc taa gtg ctg ctg ata gtt ttt gtt      384
Glu Arg His Ser Glu Ile Ala Val  *  Val Leu Leu Ile Val Phe Val
        110                 115                     120

gag ctt                                                               390
Glu Leu


<210> SEQ ID NO 13
<211> LENGTH: 124
<212> TYPE: PRT
<213> ORGANISM: Mycobacterium leprae

<400> SEQUENCE: 13

Trp Arg Ala Ala Gln Ile Pro Arg Pro Val Phe Leu Thr Asp Asp Asn
1               5                   10                  15
```

-continued

```
Val Ala Ser Val Thr Leu Thr Lys His Ser Glu Leu Leu Leu Arg Ala
            20                  25                  30

Ala Glu Phe Gly Leu Ala Met Asp Leu Thr Glu Pro Arg Glu Ala Ile
        35                  40                  45

Asn Val Cys Tyr Val Glu Met Glu Arg Glu Leu Ala His Val Leu Gly
    50                  55                  60

Asp Val Pro Gln Glu Cys Gly Thr Leu Thr Glu Phe Asp Arg Lys Val
65                  70                  75                  80

Asp His His Ala Leu His Asp Asp Asn Thr Val Gln Leu Ala Asn Leu
                85                  90                  95

Phe Glu Glu Thr Arg Phe Ile His Val Met Asn Glu Arg His Ser Glu
            100                 105                 110

Ile Ala Val Val Leu Leu Ile Val Phe Val Glu Leu
        115                 120


<210> SEQ ID NO 14
<211> LENGTH: 960
<212> TYPE: DNA
<213> ORGANISM: Mycobacterium  bovis
<220> FEATURE:
<221> NAME/KEY: CDS
<222> LOCATION: (1)...(957)

<400> SEQUENCE: 14

atg ccc ggt act aag ccc ggt agt gac aaa ccg aca ggg cgc gtc gtc       48
Met Pro Gly Thr Lys Pro Gly Ser Asp Lys Pro Thr Gly Arg Val Val
1               5                   10                  15

gtc gtg atc gtg ctc ttg atg ctt gct ggc gct gcc ctg cgc ggc cac       96
Val Val Ile Val Leu Leu Met Leu Ala Gly Ala Ala Leu Arg Gly His
            20                  25                  30

ctg ccg gcc gac gac ggt gca ccg ctc gcg gcg gcc ggc ggc agc cgg      144
Leu Pro Ala Asp Asp Gly Ala Pro Leu Ala Ala Ala Gly Gly Ser Arg
        35                  40                  45

gcg gcg ctg atg ttc att gtc gcc gca ctt gcc gcg acg ctc gcg ctg      192
Ala Ala Leu Met Phe Ile Val Ala Ala Leu Ala Ala Thr Leu Ala Leu
    50                  55                  60

ata gcg ctc gcc atc atc acc cgg ttg cga cat ccg ctc ccg gtg gcg      240
Ile Ala Leu Ala Ile Ile Thr Arg Leu Arg His Pro Leu Pro Val Ala
65                  70                  75                  80

ccc agc gcg ggg gag ctc tcg gca atg ctt ggc ggt gca gca ggg cgt      288
Pro Ser Ala Gly Glu Leu Ser Ala Met Leu Gly Gly Ala Ala Gly Arg
                85                  90                  95

ccg aac tgg cgt gtg ctg ttg ctc gga ctc ggg aca atc ctg gcc tgg      336
Pro Asn Trp Arg Val Leu Leu Leu Gly Leu Gly Thr Ile Leu Ala Trp
            100                 105                 110

ctg ctg att gcg ata ctg ctg gca cgg ttg ttc gtc ccc gat gat gtc      384
Leu Leu Ile Ala Ile Leu Leu Ala Arg Leu Phe Val Pro Asp Asp Val
        115                 120                 125

ggt cct gct gcg ccc ata ccg gat tca acc gct acg ccg gat gct tcc      432
Gly Pro Ala Ala Pro Ile Pro Asp Ser Thr Ala Thr Pro Asp Ala Ser
    130                 135                 140

agc acc acg ccg tcg cgc ccg caa ccg ccg caa gac aac aat gac gac      480
Ser Thr Thr Pro Ser Arg Pro Gln Pro Pro Gln Asp Asn Asn Asp Asp
145                 150                 155                 160

gtg ctc ggc att ctc ttt gcc agc aca atc ggc ctg ttc ttg atg gtc      528
Val Leu Gly Ile Leu Phe Ala Ser Thr Ile Gly Leu Phe Leu Met Val
                165                 170                 175

gtc gcg ggg tcg ctg att acc tcg cga cga cag cgc aag tcg gca ccg      576
Val Ala Gly Ser Leu Ile Thr Ser Arg Arg Gln Arg Lys Ser Ala Pro
            180                 185                 190
```

-continued

```
gct cgt atc agt ggc gat cgc atc gag tct ccg gcg ccc tcg gcg cgt      624
Ala Arg Ile Ser Gly Asp Arg Ile Glu Ser Pro Ala Pro Ser Ala Arg
        195                 200                 205

tcg gaa tca ctg gcg cgt gcc gcc gag atc gga ctg gcc gag atg gcc      672
Ser Glu Ser Leu Ala Arg Ala Ala Glu Ile Gly Leu Ala Glu Met Ala
    210                 215                 220

gac ctc cgc cgc gaa cca cgg gag gcg ata att gcg tgt tac gtg gcg      720
Asp Leu Arg Arg Glu Pro Arg Glu Ala Ile Ile Ala Cys Tyr Val Ala
225                 230                 235                 240

atg gag cgt gaa ctg tcg cat gtt ccc ggt gtt gcc cct cag gac ttc      768
Met Glu Arg Glu Leu Ser His Val Pro Gly Val Ala Pro Gln Asp Phe
                245                 250                 255

gac acc ccg acc gag gtg ctg gcc cga gcc gtc gaa cac cgt gcg ctc      816
Asp Thr Pro Thr Glu Val Leu Ala Arg Ala Val Glu His Arg Ala Leu
            260                 265                 270

cat ggt gct agt gcc gcc gcg ttg gtg agc ctg ttc gcc gag gcg cgt      864
His Gly Ala Ser Ala Ala Ala Leu Val Ser Leu Phe Ala Glu Ala Arg
        275                 280                 285

ttt agc ccg cac gtg atg aac gag gag cac cgt gag gtg gcg atg cgt      912
Phe Ser Pro His Val Met Asn Glu Glu His Arg Glu Val Ala Met Arg
    290                 295                 300

ttg ctt cga ctg gtt ctt gac gaa ctg agc act cgg acc gct ata          957
Leu Leu Arg Leu Val Leu Asp Glu Leu Ser Thr Arg Thr Ala Ile
305                 310                 315

tga                                                                  960


<210> SEQ ID NO 15
<211> LENGTH: 319
<212> TYPE: PRT
<213> ORGANISM: Mycobacterium bovis

<400> SEQUENCE: 15

Met Pro Gly Thr Lys Pro Gly Ser Asp Lys Pro Thr Gly Arg Val Val
1               5                   10                  15

Val Val Ile Val Leu Leu Met Leu Ala Gly Ala Ala Leu Arg Gly His
            20                  25                  30

Leu Pro Ala Asp Asp Gly Ala Pro Leu Ala Ala Ala Gly Gly Ser Arg
        35                  40                  45

Ala Ala Leu Met Phe Ile Val Ala Ala Leu Ala Ala Thr Leu Ala Leu
    50                  55                  60

Ile Ala Leu Ala Ile Ile Thr Arg Leu Arg His Pro Leu Pro Val Ala
65                  70                  75                  80

Pro Ser Ala Gly Glu Leu Ser Ala Met Leu Gly Gly Ala Ala Gly Arg
                85                  90                  95

Pro Asn Trp Arg Val Leu Leu Leu Gly Leu Gly Thr Ile Leu Ala Trp
            100                 105                 110

Leu Leu Ile Ala Ile Leu Leu Ala Arg Leu Phe Val Pro Asp Asp Val
        115                 120                 125

Gly Pro Ala Ala Pro Ile Pro Asp Ser Thr Ala Thr Pro Asp Ala Ser
    130                 135                 140

Ser Thr Thr Pro Ser Arg Pro Gln Pro Pro Gln Asp Asn Asn Asp Asp
145                 150                 155                 160

Val Leu Gly Ile Leu Phe Ala Ser Thr Ile Gly Leu Phe Leu Met Val
                165                 170                 175

Val Ala Gly Ser Leu Ile Thr Ser Arg Arg Gln Arg Lys Ser Ala Pro
            180                 185                 190
```

-continued

```
Ala Arg Ile Ser Gly Asp Arg Ile Glu Ser Pro Ala Pro Ser Ala Arg
        195                 200                 205

Ser Glu Ser Leu Ala Arg Ala Ala Glu Ile Gly Leu Ala Glu Met Ala
    210                 215                 220

Asp Leu Arg Arg Glu Pro Arg Glu Ala Ile Ile Ala Cys Tyr Val Ala
225                 230                 235                 240

Met Glu Arg Glu Leu Ser His Val Pro Gly Val Ala Pro Gln Asp Phe
                245                 250                 255

Asp Thr Pro Thr Glu Val Leu Ala Arg Ala Val Glu His Arg Ala Leu
            260                 265                 270

His Gly Ala Ser Ala Ala Ala Leu Val Ser Leu Phe Ala Glu Ala Arg
        275                 280                 285

Phe Ser Pro His Val Met Asn Glu Glu His Arg Glu Val Ala Met Arg
    290                 295                 300

Leu Leu Arg Leu Val Leu Asp Glu Leu Ser Thr Arg Thr Ala Ile
305                 310                 315


<210> SEQ ID NO 16
<211> LENGTH: 378
<212> TYPE: DNA
<213> ORGANISM: Mycobacterium bovis
<220> FEATURE:
<221> NAME/KEY: CDS
<222> LOCATION: (1)...(378)

<400> SEQUENCE: 16

cgc aag tcg gca ccg gct cgt atc agt ggc gat cgc atc gag tct ccg       48
Arg Lys Ser Ala Pro Ala Arg Ile Ser Gly Asp Arg Ile Glu Ser Pro
1               5                   10                  15

gcg ccc tcg gcg cgt tcg gaa tca ctg gcg cgt gcc gcc gag atc gga       96
Ala Pro Ser Ala Arg Ser Glu Ser Leu Ala Arg Ala Ala Glu Ile Gly
            20                  25                  30

ctg gcc gag atg gcc gac ctc cgc cgc gaa cca cgg gag gcg ata att      144
Leu Ala Glu Met Ala Asp Leu Arg Arg Glu Pro Arg Glu Ala Ile Ile
        35                  40                  45

gcg tgt tac gtg gcg atg gag cgt gaa ctg tcg cat gtt ccc ggt gtt      192
Ala Cys Tyr Val Ala Met Glu Arg Glu Leu Ser His Val Pro Gly Val
    50                  55                  60

gcc cct cag gac ttc gac acc ccg acc gag gtg ctg gcc cga gcc gtc      240
Ala Pro Gln Asp Phe Asp Thr Pro Thr Glu Val Leu Ala Arg Ala Val
65                  70                  75                  80

gaa cac cgt gcg ctc cat ggt gct agt gcc gcc gcg ttg gtg agc ctg      288
Glu His Arg Ala Leu His Gly Ala Ser Ala Ala Ala Leu Val Ser Leu
                85                  90                  95

ttc gcc gag gcg cgt ttt agc ccg cac gtg atg aac gag gag cac cgt      336
Phe Ala Glu Ala Arg Phe Ser Pro His Val Met Asn Glu Glu His Arg
            100                 105                 110

gag gtg gcg atg cgt ttg ctt cga ctg gtt ctt gac gaa ctg              378
Glu Val Ala Met Arg Leu Leu Arg Leu Val Leu Asp Glu Leu
        115                 120                 125


<210> SEQ ID NO 17
<211> LENGTH: 126
<212> TYPE: PRT
<213> ORGANISM: Mycobacterium bovis

<400> SEQUENCE: 17

Arg Lys Ser Ala Pro Ala Arg Ile Ser Gly Asp Arg Ile Glu Ser Pro
1               5                   10                  15

Ala Pro Ser Ala Arg Ser Glu Ser Leu Ala Arg Ala Ala Glu Ile Gly
```

-continued

```
            20                  25                  30

Leu Ala Glu Met Ala Asp Leu Arg Arg Glu Pro Arg Glu Ala Ile Ile
        35                  40                  45

Ala Cys Tyr Val Ala Met Glu Arg Glu Leu Ser His Val Pro Gly Val
    50                  55                  60

Ala Pro Gln Asp Phe Asp Thr Pro Thr Glu Val Leu Ala Arg Ala Val
65                  70                  75                  80

Glu His Arg Ala Leu His Gly Ala Ser Ala Ala Ala Leu Val Ser Leu
                85                  90                  95

Phe Ala Glu Ala Arg Phe Ser Pro His Val Met Asn Glu Glu His Arg
            100                 105                 110

Glu Val Ala Met Arg Leu Leu Arg Leu Val Leu Asp Glu Leu
        115                 120                 125


<210> SEQ ID NO 18
<211> LENGTH: 930
<212> TYPE: DNA
<213> ORGANISM: Mycobacterium smegmatis
<220> FEATURE:
<221> NAME/KEY: CDS
<222> LOCATION: (1)...(927)

<400> SEQUENCE: 18

atg ccc ggt ttg cag aat gcc gcg ggg cgc gtg gcc aca gtg ctc gtg       48
Met Pro Gly Leu Gln Asn Ala Ala Gly Arg Val Ala Thr Val Leu Val
1               5                   10                  15

ctc atg gtg gtc gct gtc gtc gca ctg cgc ggg cat gtc ccc ggc ggc       96
Leu Met Val Val Ala Val Val Ala Leu Arg Gly His Val Pro Gly Gly
            20                  25                  30

agc cgc gcc cag gcg cag gca ccc acc gat tct ccg gcc acg ttc gtg      144
Ser Arg Ala Gln Ala Gln Ala Pro Thr Asp Ser Pro Ala Thr Phe Val
        35                  40                  45

gcc gtc gcg gcg ctt ctc acg gtg ggg ttg gca ggc ttt gcg ttc gcg      192
Ala Val Ala Ala Leu Leu Thr Val Gly Leu Ala Gly Phe Ala Phe Ala
    50                  55                  60

att ttc acc gca ccg cgc aag ccc cgc gta tcc ggt gcc ggc gac gac      240
Ile Phe Thr Ala Pro Arg Lys Pro Arg Val Ser Gly Ala Gly Asp Asp
65                  70                  75                  80

atc ccc cag gcc ggt cta cgg ggg cca cgg gcg cgt ctg cgg tgg cga      288
Ile Pro Gln Ala Gly Leu Arg Gly Pro Arg Ala Arg Leu Arg Trp Arg
                85                  90                  95

tgg gta ctg ctg ggc ctg gcg gtc ctg atg tgc tgg ctg tcg gtc gcg      336
Trp Val Leu Leu Gly Leu Ala Val Leu Met Cys Trp Leu Ser Val Ala
            100                 105                 110

gtc ctg atc tcc cgg ttg acc gac acg tct gaa ctg ccc ccg ccc cag      384
Val Leu Ile Ser Arg Leu Thr Asp Thr Ser Glu Leu Pro Pro Pro Gln
        115                 120                 125

gac gga tcc ggg cgt gaa agc ccg ggc gcg ccg ggc gag gcc cgg gta      432
Asp Gly Ser Gly Arg Glu Ser Pro Gly Ala Pro Gly Glu Ala Arg Val
    130                 135                 140

ccc gat gat cct ggg gac gcc acc gcg ttc cgc ctg ctc gcg gtg gcc      480
Pro Asp Asp Pro Gly Asp Ala Thr Ala Phe Arg Leu Leu Ala Val Ala
145                 150                 155                 160

ggg gtg atc atg ttg ctg ctc atc gcg atc ggg acc atc ctg cgc gcc      528
Gly Val Ile Met Leu Leu Leu Ile Ala Ile Gly Thr Ile Leu Arg Ala
                165                 170                 175

agg cgc cgc gcc gcg gcc cac ctg cac cgg gcc gac gac acc tgg ccg      576
Arg Arg Arg Ala Ala Ala His Leu His Arg Ala Asp Asp Thr Trp Pro
            180                 185                 190
```

-continued

```
gtc ctg ccg gtt cac ccc aga aac ccg gag aag ctg gtc cgc gca acc      624
Val Leu Pro Val His Pro Arg Asn Pro Glu Lys Leu Val Arg Ala Thr
        195                 200                 205

gaa ctc ggg ctc gcc gag atc ggg gat ctc agc cgc gac ccc aga acc      672
Glu Leu Gly Leu Ala Glu Ile Gly Asp Leu Ser Arg Asp Pro Arg Thr
    210                 215                 220

gcg atc atc gcg tgc tat gcg gcc atg gaa cag ggc ctc gcg tac gca      720
Ala Ile Ile Ala Cys Tyr Ala Ala Met Glu Gln Gly Leu Ala Tyr Ala
225                 230                 235                 240

ccg gaa gcg gtc ccg cag gaa tcc gac aca ccg tcg gag gtg ctc gcc      768
Pro Glu Ala Val Pro Gln Glu Ser Asp Thr Pro Ser Glu Val Leu Ala
                245                 250                 255

cgt gcg gtc gag cat cac gcg ctg aat gcc gac agc gca acc gaa ctc      816
Arg Ala Val Glu His His Ala Leu Asn Ala Asp Ser Ala Thr Glu Leu
            260                 265                 270

gtc gag ctg ttc gcc gag gcg cgg ttc agc ccg cac cgg atg acc gag      864
Val Glu Leu Phe Ala Glu Ala Arg Phe Ser Pro His Arg Met Thr Glu
        275                 280                 285

acg cat cgc gcg gcc gcg gtc gcc gcg ctg cag cgc gta cac gcc gat      912
Thr His Arg Ala Ala Ala Val Ala Ala Leu Gln Arg Val His Ala Asp
    290                 295                 300

ctg cgg agc ctc gta tga                                              930
Leu Arg Ser Leu Val
305


<210> SEQ ID NO 19
<211> LENGTH: 309
<212> TYPE: PRT
<213> ORGANISM: Mycobacterium smegmatis

<400> SEQUENCE: 19

Met Pro Gly Leu Gln Asn Ala Ala Gly Arg Val Ala Thr Val Leu Val
1               5                   10                  15

Leu Met Val Val Ala Val Val Ala Leu Arg Gly His Val Pro Gly Gly
            20                  25                  30

Ser Arg Ala Gln Ala Gln Ala Pro Thr Asp Ser Pro Ala Thr Phe Val
        35                  40                  45

Ala Val Ala Ala Leu Leu Thr Val Gly Leu Ala Gly Phe Ala Phe Ala
    50                  55                  60

Ile Phe Thr Ala Pro Arg Lys Pro Arg Val Ser Gly Ala Gly Asp Asp
65                  70                  75                  80

Ile Pro Gln Ala Gly Leu Arg Gly Pro Arg Ala Arg Leu Arg Trp Arg
                85                  90                  95

Trp Val Leu Leu Gly Leu Ala Val Leu Met Cys Trp Leu Ser Val Ala
            100                 105                 110

Val Leu Ile Ser Arg Leu Thr Asp Thr Ser Glu Leu Pro Pro Pro Gln
        115                 120                 125

Asp Gly Ser Gly Arg Glu Ser Pro Gly Ala Pro Gly Glu Ala Arg Val
    130                 135                 140

Pro Asp Asp Pro Gly Asp Ala Thr Ala Phe Arg Leu Leu Ala Val Ala
145                 150                 155                 160

Gly Val Ile Met Leu Leu Leu Ile Ala Ile Gly Thr Ile Leu Arg Ala
                165                 170                 175

Arg Arg Arg Ala Ala Ala His Leu His Arg Ala Asp Asp Thr Trp Pro
            180                 185                 190

Val Leu Pro Val His Pro Arg Asn Pro Glu Lys Leu Val Arg Ala Thr
        195                 200                 205
```

-continued

```
Glu Leu Gly Leu Ala Glu Ile Gly Asp Leu Ser Arg Asp Pro Arg Thr
    210                 215                 220

Ala Ile Ile Ala Cys Tyr Ala Ala Met Glu Gln Gly Leu Ala Tyr Ala
225                 230                 235                 240

Pro Glu Ala Val Pro Gln Glu Ser Asp Thr Pro Ser Glu Val Leu Ala
                245                 250                 255

Arg Ala Val Glu His His Ala Leu Asn Ala Asp Ser Ala Thr Glu Leu
            260                 265                 270

Val Glu Leu Phe Ala Glu Ala Arg Phe Ser Pro His Arg Met Thr Glu
        275                 280                 285

Thr His Arg Ala Ala Ala Val Ala Ala Leu Gln Arg Val His Ala Asp
    290                 295                 300

Leu Arg Ser Leu Val
305


<210> SEQ ID NO 20
<211> LENGTH: 378
<212> TYPE: DNA
<213> ORGANISM: Mycobacterium smegmatis
<220> FEATURE:
<221> NAME/KEY: CDS
<222> LOCATION: (1)...(378)

<400> SEQUENCE: 20

gcc gcg gcc cac ctg cac cgg gcc gac gac acc tgg ccg gtc ctg ccg       48
Ala Ala Ala His Leu His Arg Ala Asp Asp Thr Trp Pro Val Leu Pro
1               5                   10                  15

gtt cac ccc aga aac ccg gag aag ctg gtc cgc gca acc gaa ctc ggg       96
Val His Pro Arg Asn Pro Glu Lys Leu Val Arg Ala Thr Glu Leu Gly
            20                  25                  30

ctc gcc gag atc ggg gat ctc agc cgc gac ccc aga acc gcg atc atc      144
Leu Ala Glu Ile Gly Asp Leu Ser Arg Asp Pro Arg Thr Ala Ile Ile
        35                  40                  45

gcg tgc tat gcg gcc atg gaa cag ggc ctc gcg tac gca ccg gaa gcg      192
Ala Cys Tyr Ala Ala Met Glu Gln Gly Leu Ala Tyr Ala Pro Glu Ala
    50                  55                  60

gtc ccg cag gaa tcc gac aca ccg tcg gag gtg ctc gcc cgt gcg gtc      240
Val Pro Gln Glu Ser Asp Thr Pro Ser Glu Val Leu Ala Arg Ala Val
65                  70                  75                  80

gag cat cac gcg ctg aat gcc gac agc gca acc gaa ctc gtc gag ctg      288
Glu His His Ala Leu Asn Ala Asp Ser Ala Thr Glu Leu Val Glu Leu
                85                  90                  95

ttc gcc gag gcg cgg ttc agc ccg cac cgg atg acc gag acg cat cgc      336
Phe Ala Glu Ala Arg Phe Ser Pro His Arg Met Thr Glu Thr His Arg
            100                 105                 110

gcg gcc gcg gtc gcc gcg ctg cag cgc gta cac gcc gat ctg              378
Ala Ala Ala Val Ala Ala Leu Gln Arg Val His Ala Asp Leu
        115                 120                 125


<210> SEQ ID NO 21
<211> LENGTH: 126
<212> TYPE: PRT
<213> ORGANISM: Mycobacterium smegmatis

<400> SEQUENCE: 21

Ala Ala Ala His Leu His Arg Ala Asp Asp Thr Trp Pro Val Leu Pro
1               5                   10                  15

Val His Pro Arg Asn Pro Glu Lys Leu Val Arg Ala Thr Glu Leu Gly
            20                  25                  30

Leu Ala Glu Ile Gly Asp Leu Ser Arg Asp Pro Arg Thr Ala Ile Ile
```

-continued

```
        35                  40                  45

Ala Cys Tyr Ala Ala Met Glu Gln Gly Leu Ala Tyr Ala Pro Glu Ala
    50                  55                  60

Val Pro Gln Glu Ser Asp Thr Pro Ser Glu Val Leu Ala Arg Ala Val
65                  70                  75                  80

Glu His His Ala Leu Asn Ala Asp Ser Ala Thr Glu Leu Val Glu Leu
                85                  90                  95

Phe Ala Glu Ala Arg Phe Ser Pro His Arg Met Thr Glu Thr His Arg
            100                 105                 110

Ala Ala Ala Val Ala Ala Leu Gln Arg Val His Ala Asp Leu
        115                 120                 125


<210> SEQ ID NO 22
<211> LENGTH: 1120
<212> TYPE: DNA
<213> ORGANISM: Streptomyces coelicolor
<220> FEATURE:
<221> NAME/KEY: CDS
<222> LOCATION: (104)...(1117)

<400> SEQUENCE: 22

cgggagcgcg gggcccggct cgtcggcggc tgctgccggg tgggcccgga gacgatcacg      60

tcgatcgcgc gggccctgcc ccgggagtga ccggtgcggc gtg tgc caa gat tgc       115
                                                Cys Gln Asp Cys
                                                1

cgt gaa cag gcg ttc ggg ggc ggc gac ggg ttc ggc ggg ggg cac ggc       163
Arg Glu Gln Ala Phe Gly Gly Gly Asp Gly Phe Gly Gly Gly His Gly
5                   10                  15                  20

atg gga cgc ggg ggg cgg acg gga cac ggg gtg gca ccg ggg gtg ctg       211
Met Gly Arg Gly Gly Arg Thr Gly His Gly Val Ala Pro Gly Val Leu
                25                  30                  35

gtc gcc gcc gcg gtg gtc ggg acg ctg gcc gtc gcc gcg ctc gcg ctg       259
Val Ala Ala Ala Val Val Gly Thr Leu Ala Val Ala Ala Leu Ala Leu
            40                  45                  50

cgg ccc gcg cag ggg ttg ctc cac tcc ggc cgg ggt ccg ctc ggt cac       307
Arg Pro Ala Gln Gly Leu Leu His Ser Gly Arg Gly Pro Leu Gly His
        55                  60                  65

tgg ggt ttc gtg gcg atc ggg gcg tcc gtc gcc tgg acc ttc ggg acc       355
Trp Gly Phe Val Ala Ile Gly Ala Ser Val Ala Trp Thr Phe Gly Thr
    70                  75                  80

tgg acg gtc gta cag cgt ctt cgc ccc cgt ttc ggc gcc gac cgc ctt       403
Trp Thr Val Val Gln Arg Leu Arg Pro Arg Phe Gly Ala Asp Arg Leu
85                  90                  95                  100

tcg ctg ccg ccg ggt gag gag cgg ctg cgg gaa gcc gcc gcg ccc ctg       451
Ser Leu Pro Pro Gly Glu Glu Arg Leu Arg Glu Ala Ala Ala Pro Leu
                105                 110                 115

ctg ctc gcc gcg acg ggc gtc atc ggc gtc ctg gcc ctg gtc ctg cac       499
Leu Leu Ala Ala Thr Gly Val Ile Gly Val Leu Ala Leu Val Leu His
            120                 125                 130

cgg ttc tcc acc ggc ggc aac acg acc ggc ccg ccc ccg ccc ctg gcg       547
Arg Phe Ser Thr Gly Gly Asn Thr Thr Gly Pro Pro Pro Pro Leu Ala
        135                 140                 145

cgg gag ccg gcc ccc acg ccg acc ttc ctc act ccc ccg ccc cag cag       595
Arg Glu Pro Ala Pro Thr Pro Thr Phe Leu Thr Pro Pro Pro Gln Gln
    150                 155                 160

cgg cac ggt tcg acg gac cac tcc tcc ctg ccg ctg tac ctc gtg ctc       643
Arg His Gly Ser Thr Asp His Ser Ser Leu Pro Leu Tyr Leu Val Leu
165                 170                 175                 180

gcg ttg ctg gcc gcg gtc gcc gtc gtg gtc gtc gtg gtg gcc gtc gtg       691
```

-continued

```
Ala Leu Leu Ala Ala Val Ala Val Val Val Val Val Val Ala Val Val
                185                 190                 195

cgg cgg ctg cga cgg ttc ggc atg cgg gtg ccg cag cgt ccc ggc cct      739
Arg Arg Leu Arg Arg Phe Gly Met Arg Val Pro Gln Arg Pro Gly Pro
            200                 205                 210

ccg ggc acc gtc gcg cag gac gac gac gcg cgg ctg ctg ctg tcc gcc      787
Pro Gly Thr Val Ala Gln Asp Asp Asp Ala Arg Leu Leu Leu Ser Ala
        215                 220                 225

gtg gac tcg ggc cgc cgc gcc ctg gcc ggc acg gat gac gac gcc cgg      835
Val Asp Ser Gly Arg Arg Ala Leu Ala Gly Thr Asp Asp Asp Ala Arg
    230                 235                 240

gcg gcc gtc atc gcc tgt tac gcc gcg atg gag gac gcc ctc gcg gcg      883
Ala Ala Val Ile Ala Cys Tyr Ala Ala Met Glu Asp Ala Leu Ala Ala
245                 250                 255                 260

tcc ggt gtg ccg cgg cac gcc tcc gac agc ccc gcc gac ctg ctc acc      931
Ser Gly Val Pro Arg His Ala Ser Asp Ser Pro Ala Asp Leu Leu Thr
                265                 270                 275

cgc gct gcc ggc acg ggc ttc gcc ccg ggc ccg gcc gcg ccg cgt ctg      979
Arg Ala Ala Gly Thr Gly Phe Ala Pro Gly Pro Ala Ala Pro Arg Leu
            280                 285                 290

acc gcg ctg ttc cgc gag gcc cgt tac tcc tcg cac ccg atg gac ggc     1027
Thr Ala Leu Phe Arg Glu Ala Arg Tyr Ser Ser His Pro Met Asp Gly
        295                 300                 305

tcg cac cgg aag gcc gcg gcc gac gcg ctg gag gag atc gcc tcc ctg     1075
Ser His Arg Lys Ala Ala Ala Asp Ala Leu Glu Glu Ile Ala Ser Leu
    310                 315                 320

ctg cgg gac cgt gac gcg gac gcg gtc cgg gag gcc ggg cgg             1117
Leu Arg Asp Arg Asp Ala Asp Ala Val Arg Glu Ala Gly Arg
325                 330                 335

tga                                                                 1120


<210> SEQ ID NO 23
<211> LENGTH: 338
<212> TYPE: PRT
<213> ORGANISM: Streptomyces coelicolor

<400> SEQUENCE: 23

Cys Gln Asp Cys Arg Glu Gln Ala Phe Gly Gly Gly Asp Gly Phe Gly
1               5                   10                  15

Gly Gly His Gly Met Gly Arg Gly Gly Arg Thr Gly His Gly Val Ala
            20                  25                  30

Pro Gly Val Leu Val Ala Ala Ala Val Val Gly Thr Leu Ala Val Ala
        35                  40                  45

Ala Leu Ala Leu Arg Pro Ala Gln Gly Leu Leu His Ser Gly Arg Gly
    50                  55                  60

Pro Leu Gly His Trp Gly Phe Val Ala Ile Gly Ala Ser Val Ala Trp
65                  70                  75                  80

Thr Phe Gly Thr Trp Thr Val Val Gln Arg Leu Arg Pro Arg Phe Gly
                85                  90                  95

Ala Asp Arg Leu Ser Leu Pro Pro Gly Glu Glu Arg Leu Arg Glu Ala
            100                 105                 110

Ala Ala Pro Leu Leu Leu Ala Ala Thr Gly Val Ile Gly Val Leu Ala
        115                 120                 125

Leu Val Leu His Arg Phe Ser Thr Gly Gly Asn Thr Thr Gly Pro Pro
    130                 135                 140

Pro Pro Leu Ala Arg Glu Pro Ala Pro Thr Pro Thr Phe Leu Thr Pro
145                 150                 155                 160
```

-continued

```
Pro Pro Gln Gln Arg His Gly Ser Thr Asp His Ser Ser Leu Pro Leu
                165                 170                 175

Tyr Leu Val Leu Ala Leu Leu Ala Ala Val Ala Val Val Val Val Val
            180                 185                 190

Val Ala Val Val Arg Arg Leu Arg Arg Phe Gly Met Arg Val Pro Gln
        195                 200                 205

Arg Pro Gly Pro Pro Gly Thr Val Ala Gln Asp Asp Asp Ala Arg Leu
    210                 215                 220

Leu Leu Ser Ala Val Asp Ser Gly Arg Arg Ala Leu Ala Gly Thr Asp
225                 230                 235                 240

Asp Asp Ala Arg Ala Ala Val Ile Ala Cys Tyr Ala Ala Met Glu Asp
                245                 250                 255

Ala Leu Ala Ala Ser Gly Val Pro Arg His Ala Ser Asp Ser Pro Ala
            260                 265                 270

Asp Leu Leu Thr Arg Ala Ala Gly Thr Gly Phe Ala Pro Gly Pro Ala
        275                 280                 285

Ala Pro Arg Leu Thr Ala Leu Phe Arg Glu Ala Arg Tyr Ser Ser His
    290                 295                 300

Pro Met Asp Gly Ser His Arg Lys Ala Ala Ala Asp Ala Leu Glu Glu
305                 310                 315                 320

Ile Ala Ser Leu Leu Arg Asp Arg Asp Ala Asp Ala Val Arg Glu Ala
                325                 330                 335

Gly Arg


<210> SEQ ID NO 24
<211> LENGTH: 378
<212> TYPE: DNA
<213> ORGANISM: Streptomyces coelicolor
<220> FEATURE:
<221> NAME/KEY: CDS
<222> LOCATION: (1)...(378)

<400> SEQUENCE: 24

cga cgg ttc ggc atg cgg gtg ccg cag cgt ccc ggc cct ccg ggc acc       48
Arg Arg Phe Gly Met Arg Val Pro Gln Arg Pro Gly Pro Pro Gly Thr
1               5                   10                  15

gtc gcg cag gac gac gac gcg cgg ctg ctg ctg tcc gcc gtg gac tcg       96
Val Ala Gln Asp Asp Asp Ala Arg Leu Leu Leu Ser Ala Val Asp Ser
            20                  25                  30

ggc cgc cgc gcc ctg gcc ggc acg gat gac gac gcc cgg gcg gcc gtc      144
Gly Arg Arg Ala Leu Ala Gly Thr Asp Asp Asp Ala Arg Ala Ala Val
        35                  40                  45

atc gcc tgt tac gcc gcg atg gag gac gcc ctc gcg gcg tcc ggt gtg      192
Ile Ala Cys Tyr Ala Ala Met Glu Asp Ala Leu Ala Ala Ser Gly Val
    50                  55                  60

ccg cgg cac gcc tcc gac agc ccc gcc gac ctg ctc acc cgc gct gcc      240
Pro Arg His Ala Ser Asp Ser Pro Ala Asp Leu Leu Thr Arg Ala Ala
65                  70                  75                  80

ggc acg ggc ttc gcc ccg ggc ccg gcc gcg ccg cgt ctg acc gcg ctg      288
Gly Thr Gly Phe Ala Pro Gly Pro Ala Ala Pro Arg Leu Thr Ala Leu
                85                  90                  95

ttc cgc gag gcc cgt tac tcc tcg cac ccg atg gac ggc tcg cac cgg      336
Phe Arg Glu Ala Arg Tyr Ser Ser His Pro Met Asp Gly Ser His Arg
            100                 105                 110

aag gcc gcg gcc gac gcg ctg gag gag atc gcc tcc ctg ctg              378
Lys Ala Ala Ala Asp Ala Leu Glu Glu Ile Ala Ser Leu Leu
        115                 120                 125
```

-continued

<210> SEQ ID NO 25
<211> LENGTH: 126
<212> TYPE: PRT
<213> ORGANISM: Streptomyces coelicolor

<400> SEQUENCE: 25

```
Arg Arg Phe Gly Met Arg Val Pro Gln Arg Pro Gly Pro Pro Gly Thr
1               5                   10                  15

Val Ala Gln Asp Asp Asp Ala Arg Leu Leu Leu Ser Ala Val Asp Ser
            20                  25                  30

Gly Arg Arg Ala Leu Ala Gly Thr Asp Asp Asp Ala Arg Ala Ala Val
        35                  40                  45

Ile Ala Cys Tyr Ala Ala Met Glu Asp Ala Leu Ala Ala Ser Gly Val
    50                  55                  60

Pro Arg His Ala Ser Asp Ser Pro Ala Asp Leu Leu Thr Arg Ala Ala
65                  70                  75                  80

Gly Thr Gly Phe Ala Pro Gly Pro Ala Ala Pro Arg Leu Thr Ala Leu
                85                  90                  95

Phe Arg Glu Ala Arg Tyr Ser Ser His Pro Met Asp Gly Ser His Arg
            100                 105                 110

Lys Ala Ala Ala Asp Ala Leu Glu Glu Ile Ala Ser Leu Leu
        115                 120                 125
```

<210> SEQ ID NO 26
<211> LENGTH: 99
<212> TYPE: PRT
<213> ORGANISM: Artificial Sequence
<220> FEATURE:
<223> OTHER INFORMATION: synthetic construct

<400> SEQUENCE: 26

```
Leu Arg Arg Ala Gly Asp Glu Leu Glu Lys Arg Tyr Glu Arg Val Phe
1               5                   10                  15

Ser Ser Met Ala Val Gln Leu His Ile Thr Pro Glu Thr Ala Arg Glu
            20                  25                  30

Leu Phe Thr Gln Val Ala Gly Glu Leu Phe Ser Asp Gly Ile Asn Trp
        35                  40                  45

Gly Arg Ile Val Ala Leu Phe Ser Phe Gly Gly Ala Leu Ala Lys Lys
    50                  55                  60

Leu Val Asn Ser Ala Met Glu Gly Leu Val Ser Arg Leu Ala Asp Trp
65                  70                  75                  80

Met Val Glu Phe Leu Lys His Asn Leu Ala Glu Trp Ile Gln Gln Asn
                85                  90                  95

Gly Gly Trp
```

<210> SEQ ID NO 27
<211> LENGTH: 99
<212> TYPE: PRT
<213> ORGANISM: Homo sapiens

<400> SEQUENCE: 27

```
Leu Arg Gln Ala Gly Asp Asp Phe Ser Arg Arg Tyr Arg Arg Asp Phe
1               5                   10                  15

Ala Glu Met Ser Ser Gln Leu His Leu Thr Pro Phe Thr Ala Arg Gly
            20                  25                  30

Arg Phe Ala Thr Val Val Glu Glu Leu Phe Arg Asp Gly Val Asn Trp
        35                  40                  45

Gly Arg Ile Val Ala Phe Phe Glu Phe Gly Gly Val Met Cys Val Glu
```

-continued

```
    50                  55                  60

Ser Val Asn Arg Glu Met Ser Pro Leu Val Asp Asn Ile Ala Leu Trp
65                  70                  75                  80

Met Thr Glu Tyr Leu Asn Arg His Leu His Thr Trp Ile Gln Asp Asn
                85                  90                  95

Gly Gly Trp


<210> SEQ ID NO 28
<211> LENGTH: 102
<212> TYPE: PRT
<213> ORGANISM: Rattus norvegicus

<400> SEQUENCE: 28

Leu Leu Arg Leu Gly Asp Glu Leu Glu Gln Ile Arg Pro Ser Val Tyr
1               5                   10                  15

Arg Asn Val Ala Arg Gln Leu His Ile Pro Leu Gln Ser Glu Pro Val
            20                  25                  30

Val Thr Asp Ala Phe Leu Ala Val Ala Gly His Ile Phe Ser Ala Gly
        35                  40                  45

Ile Thr Trp Gly Lys Val Val Ser Leu Tyr Ser Val Ala Ala Gly Leu
    50                  55                  60

Ala Val Asp Cys Val Arg Gln Ala Gln Pro Ala Met Val His Ala Leu
65                  70                  75                  80

Val Asp Cys Leu Gly Glu Phe Val Arg Lys Thr Leu Ala Thr Trp Leu
                85                  90                  95

Arg Arg Arg Gly Gly Trp
            100


<210> SEQ ID NO 29
<211> LENGTH: 92
<212> TYPE: PRT
<213> ORGANISM: Asfarviridae sp.

<400> SEQUENCE: 29

Leu Thr Tyr Tyr Asp Glu Cys Leu Asn Lys Gln Val Thr Ile Thr Phe
1               5                   10                  15

Ser Leu Thr Ser Val Gln Glu Ile Lys Thr Gln Phe Thr Gly Val Val
            20                  25                  30

Thr Glu Leu Phe Lys Asp Leu Ile Asn Trp Gly Arg Ile Cys Gly Phe
        35                  40                  45

Ile Val Phe Ser Ala Lys Met Ala Lys Tyr Cys Lys Asp Ala Asn Asn
    50                  55                  60

His Leu Glu Ser Thr Val Ile Thr Thr Ala Tyr Asn Phe Met Lys His
65                  70                  75                  80

Asn Leu Leu Pro Trp Met Ile Ser His Gly Gly Gln
                85                  90


<210> SEQ ID NO 30
<211> LENGTH: 104
<212> TYPE: PRT
<213> ORGANISM: Homo sapiens

<400> SEQUENCE: 30

Leu Gln Asn Val Ala Phe Ser Val Gln Lys Glu Val Glu Lys Asn Leu
1               5                   10                  15

Lys Ser Cys Leu Asp Asn Val Asn Val Val Ser Val Asp Thr Ala Arg
            20                  25                  30
```

-continued

```
Thr Leu Phe Asn Gln Val Met Glu Lys Glu Phe Glu Asp Gly Ile Ile
        35                  40                  45

Asn Trp Gly Arg Ile Val Thr Ile Phe Ala Phe Glu Gly Ile Leu Ile
    50                  55                  60

Lys Lys Leu Leu Arg Gln Gln Ile Ala Pro Asp Val Asp Thr Tyr Lys
65                  70                  75                  80

Glu Ile Ser Tyr Phe Val Ala Glu Phe Ile Met Asn Asn Thr Gly Glu
                85                  90                  95

Trp Ile Arg Gln Asn Gly Gly Trp
            100
```

BACTERIAL BCL-2 DOMAIN-CONTAINING POLYPEPTIDES, ENCODING NUCLEIC ACID MOLECULES, AND RELATED METHODS

This application claims benefit of the filing date of U.S. Provisional Application No. 60/332,964, filed Nov. 13, 2001, which is incorporated herein by reference.

This invention was made with United States Government support under grant number DBI-0078731 awarded by the National Science Foundation, and grant number GM60049 awarded by the National Institutes of Health. The U.S. Government has certain rights in this invention.

BACKGROUND OF THE INVENTION

1. Field of the Invention

The invention relates generally to the fields of medicine and cell biology and, more specifically, to the fields of infectious disease and regulation of apoptosis.

2. Background Information

Apoptosis, or programmed cell death, is an important process in the development and homeostasis of multicellular organisms. Additionally, apoptosis of infected cells provides the host organism with an effective defense mechanism against pathogens. Alterations in the normal process of apoptosis occur in various pathological conditions, including cancer, autoimmune diseases, degenerative syndromes and infectious diseases.

Some of the proteins involved in apoptosis have been identified, and associations among these proteins described. The principal effectors of apoptosis are a family of intracellular proteases known as caspases. Initiation of the caspase proteolytic cascade requires assembly of caspase precursors on an adaptor protein. Members of a family of proteins known as Bcl-2 proteins are key regulators of apoptosis, in part because they determine whether this adaptor/procaspase complex can form. Bcl-2 family members also regulate apoptosis by regulating mitochondrial integrity, thereby controlling release of the caspase co-activator protein cytochrome c. Bcl-2 family members have been found in organisms as diverse as mammals, nematodes, fruitflies and viruses. However, no Bcl-2 family members have been identified to date in prokaryotes.

Dysregulation of host cell apoptosis figures prominently in the pathophysiology of many bacterial infectious diseases. Some of the effects of these bacteria on the host cell apoptotic machinery have been partially elucidated for certain bacteria. However, the bacterial proteins that exert these effects remain to be identified and their mechanisms of action characterized.

A number of intracellular bacteria act by inducing host cell apoptosis, often in a cell-type specific manner. For example, *Shigella flexneri*, a causative agent of bacillary dysentery, infects macrophages and induces their apoptosis in part via activation of caspase-1. Concomitant with apoptosis is a release of inflammatory cytokines that cause migration of polymorphonuclear leukocytes across the intestinal epithelium to the site of the infection, which compromises the integrity of the epithelial barrier, promoting massive secondary invasion of the bacteria and acute inflammation. Other examples of pro-apoptotic infectious bacteria include *Salmonella, Listeria, Legionella, Yersinia* and *Coxiella*, which target various regulatory molecules in the host cell apoptotic pathway.

Certain infectious bacteria both induce and inhibit host cell apoptosis. For example, *Mycobacterium tuberculosis,* a causative agent of tuberculosis, induces apoptosis in macrophages in part by down-regulation of expression of the host anti-apoptotic protein Bcl-2. Paradoxically, *M. tuberculosis* infection also protects cells against apoptosis in part via induction of the NF-κB cell survival pathway, and also by enhancing production of soluble TNF receptor 2, which neutralizes the pro-apoptotic activity of TNFα. Both pro- and anti-apoptotic activities, which are possibly manifested during different stages of infection, may be needed for establishment of a persistent infection. Other bacteria that both induce and inhibit host cell apoptosis by various mechanisms include *Chlamydia* and *Rickettsia.*

Although apoptosis is generally considered to be a eukaryotic process, many bacteria undergo an apoptotic-like process that prevents multiplication under conditions of environmental stress. This adaptive response is particularly apparent in prokaryotic organisms that display developmental programs, such as sporulation in *Streptomyces* and *Bacillus* and the formation of nonculturable but viable cells in various Gram-negative bacteria. Similarities between eukaryotic apoptosis and the prokaryotic apoptotic-like process include induction of protein synthesis, proteolytic activity, DNA fragmentation, RNA degradation and cell shrinkage.

The development of drug resistant strains of bacteria is a serious health concern. It is currently estimated that within the next 10 years, virtually all antibiotics currently employed for treating bacterial infections will no longer be effective, due to microbial resistance. New therapeutic agents are urgently needed to meet the threat of drug-resistant bacteria. In view of the important role of apoptosis in the bacterial life cycle and in pathogenesis, there exists a need to identify bacterial molecules that regulate bacterial and host cell apoptosis. Such molecules can be used in the development of novel antibiotics, as well as in the development of therapeutic agents for the treatment of other disorders of apoptotic regulation. The present invention satisfies this need and provides related advantages as well.

SUMMARY OF THE INVENTION

The invention provides isolated Bcl-2 domain-containing polypeptides from Mycobacterial species, including *M. tuberculosis, M. avium, M. bovis, M. leprae* and *M. smegmatis,* and from *Streptomyces* species, including *S. coelicolor.* Also provided are modifications thereof, functional fragments therefrom, and isolated peptides therefrom.

The invention further provides isolated nucleic acid molecules encoding Bcl-2 domain-containing polypeptides from Mycobacterial and *Streptomyces* species, and modifications and functional fragments therefrom. Also provided are vectors and cells containing such nucleic acid molecules, isolated oligonucleotides, and related detection methods.

Also provided are antibodies and antigen-binding fragments thereof that specifically bind Bcl-2 domain-containing polypeptides from Mycobacterial and *Streptomyces* species, and related detection methods.

The invention also provides a method of identifying a polypeptide that associates with a Bcl-2 domain-containing polypeptide. The method is practiced by contacting an invention Bcl-2 domain-containing polypeptide with a candidate polypeptide, and determining association between the polypeptides.

Also provided is a method of identifying a compound that associates with a Bcl-2 domain-containing polypeptide (a B2AP). The method is practiced by contacting an invention Bcl-2 domain-containing polypeptide with a candidate compound, and determining association between the compound and the polypeptide.

Further provided is a method of identifying a compound that modulates an apoptotic activity of a Bcl-2 domain-containing polypeptide. The method is practiced by contacting an invention Bcl-2 domain-containing polypeptide with a candidate compound, and determining an apoptotic activity of said polypeptide, whereby a compound that modulates an apoptotic activity of the polypeptide is identified.

The invention also provides a method of identifying an effective agent that alters the association between a B2AP and a Bcl-2 domain-containing polypeptide. The method is practiced by contacting an invention Bcl-2 domain-containing polypeptide and a B2AP under conditions that allow the polypeptides to associate, with a candidate compound, and determining association of the polypeptide and the B2AP, wherein a compound that alters the association is identified as an effective agent.

Also provided are methods of modulating apoptosis in a cell. In one embodiment, the method is practiced by introducing an invention nucleic acid molecule into a cell, and expressing the Bcl-2 domain-containing polypeptide or functional fragment encoded by the nucleic acid molecule in the cell, whereby expression of the polypeptide modulates apoptosis. In another embodiment, the method is practiced by introducing into the cell an antisense, dsRNA or ribozyme nucleic acid molecule that specifically hybridizes to a nucleic acid molecule encoding a Mycobacterial or *Streptomyces* Bcl-2 domain-containing polypeptide. In yet another embodiment, the method is practiced by administering to the cell a compound identified by the invention screening methods. Related methods of treating a pathological condition in an individual are also provided.

DETAILED DESCRIPTION OF THE INVENTION

The invention provides bacterial molecules containing domains with structural similarity to eukaryotic Bcl-2 family members (designated herein "Bcl-2 domains"), including Bcl-2 domain-containing polypeptides, encoding nucleic acid molecules, antibodies, and related compositions. Bacterial Bcl-2 domain-containing molecules, like their eukaryotic homologs, can play important roles in positively or negatively regulating apoptosis either within the bacteria or within infected host cells. Therefore bacterial Bcl-2 domain-containing molecules, and compounds that modulate the activity of these molecules, can be used therapeutically in the treatment of infectious diseases and in other conditions in which promotion or inhibition of apoptosis is warranted.

The Bcl-2 domain is a structurally conserved domain found in many eukaryotic and viral proteins. Despite functional similarities between pro- and anti-apoptotic Bcl-2 family members, there is little overall amino acid sequence homology within the Bcl-2 domain of known proteins. The Bcl-2 domain is generally about 100-110 amino acids in length and comprises a bundle of α-helices, minimally six. The Bcl-2 domain is characterized by containing from one to four short Bcl-2 homology regions (BH1-BH4), with the BH3 and BH4 regions forming amphipathic α-helices, and the BH1 and BH2 regions consisting in part of an α-helix and a turn. The sixth helix in several Bcl-2 family members overlaps with the BH2 region.

The structures of Bcl-2 family members can readily be predicted by known methods. For example, Petros et al., *Proc. Natl. Acad. Sci.* 98:3012-3017 (2001), described the solution structure of two isoforms of human Bcl-2. The predicted boundaries of the 7 helices of human Bcl-2 are set forth in gi:14719780. Additionally, Muchmore et al., *Nature* 381: 335-341 (1996), described the crystal and solution structures of the Bcl-2 family member Bcl-$X_L$, and aligned the helices and BH domains of BCl-$X_L$ with those of five other Bcl-2 family members. Based on structural determinations and alignments known in the art, the topology and functional regions of other Bcl-2 family members can be predicted.

The BH1, BH2 and BH3 regions are involved in dimerization between Bcl-2 family members. For example, the BH3 helix of the pro-apoptotic Bcl-2 family members binds to a hydrophobic groove on the anti-apoptotic members created by α-helices in the BH3, BH1 and BH2 regions. The BH4 region is thought to mediate interactions with a variety of cellular proteins.

The characterization of a domain as a "Bcl-2 domain" can be confirmed using a Fold & Function Assignment System (FFAS) fold prediction calculation (Rychlewski et al., *Protein Sci.* 9:232-241 (2000)), using a database of proteins of known structures enriched in apoptotic domains, such as the Pfam database of Bcl-2 family members available on the World Wide Web at ncbi.nlm.nih.gov/Structure/cdd/cddsrv.cgi?uid=pfam00452&version=v1.54), as described in the Example.

Figure 1:
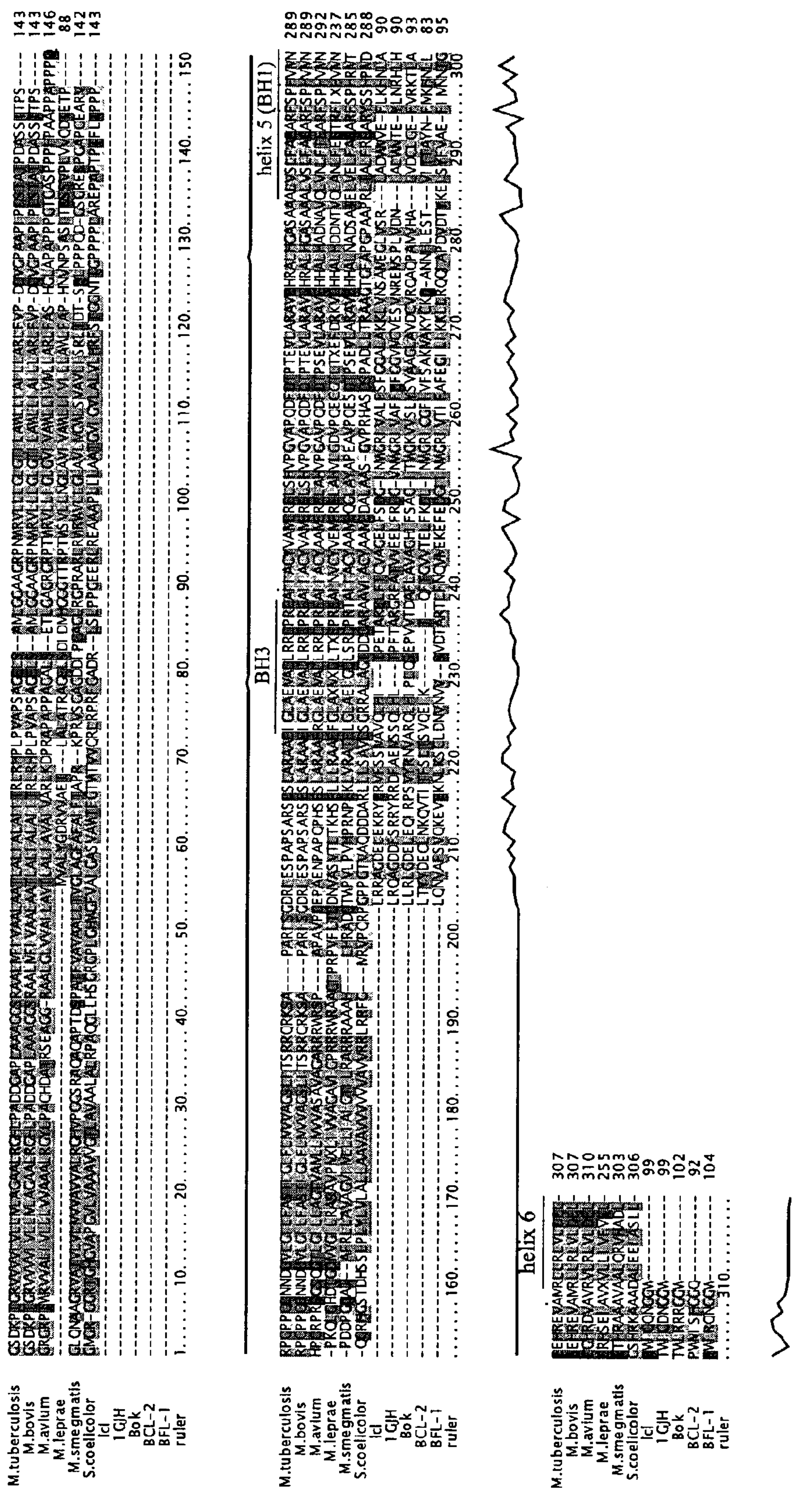
FIG. 1 shows an alignment of bacterial Bcl-2 domain-containing proteins from *M. tuberculosis* (portion of SEQ ID NO:2); *M. bovis* (portion of SEQ ID NO:15); *M. avium* (portion of SEQ ID NO:7); *M. leprae* (portion of SEQ ID NO:15); *M. smegmatis* (portion of SEQ ID NO:19); and *S. coelicolor* (portion of SEQ ID NO:23); together with five diverse Bcl-2 domain-containing proteins present in the Pfam00452 database: lcl (a consensus sequence of Bcl-2 domain-containing proteins; SEQ ID NO:26); 1GJH (Chain A, Human Bcl-2 Isoform 2, gi:14719780; SEQ ID NO:27); Bok (rat Bcl-2 related ovarian killer protein; gi:2645560; SEQ ID NO:28); BCL-2 (African swine fever virus BCL-2 homolog precursor; gi:1169456; SEQ ID NO:29), and BFL-1 (human hematopoietic-specific early response protein; gi:2493280; SEQ ID NO:30). The predicted BH3, helix 5(BH1) and helix 6 motifs within the Bcl-2 domains are overlined. The alignment was generated with CLUSTALX version 1.8.

The bacterial Bcl-2 domains herein designated SEQ ID NOS:5, 9, 13, 17, 21 and 25, described further below, all contain a BH3 region and a BH1 region. However, bacterial Bcl-2 domains can optionally further contain a BH2 and/or a BH4 region, and optionally may not contain a BH1 region. FIG. 1 shows an alignment of the Bcl-2 domains of the bacterial polypeptides disclosed herein, showing the conserved structural motifs designated BH3, helix 5 (BH1) and helix 6.

As disclosed herein, Bcl-2 domain-containing molecules are present in *Mycobacterium* species. There are more than 70 species of *Mycobacterium*, including both slowly growing and rapidly growing species, and both pathogenic and non-pathogenic species (reviewed in Shinnick et al., *Eur. J. Clin. Microb. Infect. Dis.* 13:884-901 (1994)). It is contemplated herein that any or all species in the *Mycobacterium* genus can express a Bcl-2 domain-containing polypeptide at some point in their life cycle.

Exemplary *Mycobacterium* species that are pathogenic to humans include, for example, *M. tuberculosis, M. africanum* and *M. bovis,* which cause pulmonary tuberculosis; *M. leprae,* which causes Hansen's disease; *M. avium,* which causes nontuberculous lymphadenitis; *M. genavense,* which is an opportunistic pathogen common in AIDS patients; *M. ulcerans* and *M. marinum,* which causes skin lesions; *M. kansasii,*

*M. szulgai* and *M. asiaticum,* which cause chronic pulmonary disease; *M. scrofulaceum,* which causes cervical adenitis; *M. fortuitum, M. abscessus* and *M. smegmatis,* which occur in infected skin and soft tissue wounds; and the like. Other species of Mycobacteria are known in the art that cause pulmonary, lymphatic, cutaneous and disseminated disease. As will be described further below, compounds that modulate the activity of a Mycobacterial Bcl-2 domain-containing polypeptide can be used to prevent or ameliorate the diseases caused by these pathogens in humans and other mammals.

As disclosed herein, Bcl-2 domain-containing polypeptides are also present in *Streptomyces* species. *Streptomycetes* are Gram-positive bacteria generally found in soil. *Streptomycetes* are well known for their capacity to produce a multitude of varied and complex secondary metabolites, many of which are antimicrobial substances. Certain strains of non-pathogenic, antibiotic-producing *streptomycetes* have been shown to reduce bacterial and fungal plant diseases when added to disease-conducive soil. However, other *Streptomyces* species are themselves plant pathogens, including, for example, *S. scabies, S. acidiscabies* and *S. turgidiscabies.* Although most species of *Streptomyces* are non-pathogenic in humans, several pathogenic species have been identified, which include *S. somaliensis,* which causes mycetoma, and *S. pneumonia,* which has been found in pulmonary infiltrates in immunocompromised individuals.

It is contemplated that any or all species in the *Streptomyces* genus can express a Bcl-2 domain-containing polypeptide at some point in their life cycle. Therefore, compounds that modulate the activity of a *Streptomyces* Bcl-2 domain-containing polypeptide can be used to treat *Streptomyces* infections, including infections in humans, other mammals and plants. Such compounds can also be useful to reduce apoptosis in beneficial species, such that the yield of anti-infectives and other beneficial products produced by these bacteria can be increased in commercial fermentation processes.

The invention provides isolated nucleic acid molecules encoding Bcl-2 domain-containing polypeptides. Such isolated nucleic acid molecules can be used, for example, as templates for the recombinant expression of Bcl-2 domain-containing polypeptides; in screening assays to identify cellular molecules that associate with bacterial Bcl-2 domain-containing polypeptides or compounds that promote or disrupt the function of Bcl-2 domain-containing polypeptides; as probes to detect Bcl-2 domain-encoding polypeptides in samples; in in vivo and ex vivo gene therapy applications to positively or negatively regulate bacterial proliferation and pathogenicity; and in other therapeutic, diagnostic and screening applications known to those skilled in the art.

The term "isolated," in reference to an invention nucleic acid molecule or polypeptide is intended to mean that the molecule is substantially removed or separated from components with which it is naturally associated, or is otherwise modified by the hand of man, thereby excluding nucleic acid and polypeptide molecules as they exist in nature.

The term "nucleic acid molecule," as used herein, refers to an oligonucleotide or polynucleotide of natural or synthetic origin. A nucleic acid molecule can be single- or double-stranded genomic DNA, cDNA or RNA, and can represent the sense strand, the antisense strand, or both. A nucleic acid molecule can include one or more non-native nucleotides, having, for example, modifications to the base, the sugar, or the phosphate portion, or having a modified phosphodiester linkage. Such modifications can be advantageous in increasing the stability of the nucleic acid molecule. Furthermore, a nucleic acid molecule can include, for example, a detectable moiety, such as a radiolabel, a fluorochrome, a ferromagnetic substance, a luminescent tag or a detectable binding agent such as biotin. Such modifications can be advantageous in applications where detection of a hybridizing nucleic acid molecule is desired.

In one embodiment, the invention provides an isolated nucleic acid molecule encoding a polypeptide containing a Bcl-2 domain from a *Mycobacterium* species. For example, the invention provides an isolated nucleic acid molecule encoding a polypeptide containing the Bcl-2 domain designated SEQ ID NO:5 present in the *Mycobacterium tuberculosis* strain H37RV hypothetical protein Rv3166c (gi: 7477511; designated herein "Bcl-MT"; SEQ ID NO:2 or NO:3), including an isolated nucleic acid molecule comprising the nucleotide sequence designated SEQ ID NO:4.

The invention also provides an isolated nucleic acid molecule encoding a polypeptide containing the Bcl-2 domain designated SEQ ID NO:9 present in a *Mycobacterium avium* polypeptide (designated herein "Bcl-MA"; SEQ ID NO:7), including an isolated nucleic acid molecule comprising the nucleotide sequence designated SEQ ID NO:8.

The invention further provides an isolated nucleic acid molecule encoding a polypeptide containing the Bcl-2 domain designated SEQ ID NO:13 present in a *Mycobacterium leprae* polypeptide (designated herein "Bcl-ML"; SEQ ID NO:11), including an isolated nucleic acid molecule comprising the nucleotide sequence designated SEQ ID NO:12.

The invention further provides an isolated nucleic acid molecule encoding a polypeptide containing the Bcl-2 domain designated SEQ ID NO:17 present in *Mycobacterium bovis* polypeptide (designated herein "Bcl-MB"; SEQ ID NO:15), including an isolated nucleic acid molecule comprising the nucleotide sequence designated SEQ ID NO:16.

Further provided is an isolated nucleic acid molecule encoding a polypeptide containing the Bcl-2 domain designated SEQ ID NO:25 present in *Mycobacterium smegmatis* polypeptide (designated herein "Bcl-MB"; SEQ ID NO:19), including an isolated nucleic acid molecule comprising the nucleotide sequence designated SEQ ID NO:20.

In another embodiment, the invention provides an isolated nucleic acid molecule encoding a polypeptide containing a Bcl-2 domain from a *Streptomyces* species. For example, the invention provides an isolated nucleic acid molecule encoding a polypeptide containing the Bcl-2 domain designated SEQ ID NO:25 from the *Streptomyces coelicolor* probable transmembrane protein (GI 7481597; SEQ ID NO:23; designated herein "Bcl-SC"), including an isolated nucleic acid molecule comprising the nucleotide sequence designated SEQ ID NO:24.

No significant sequence homology between the disclosed Bcl-2 domain-containing proteins of Mycobacterial species and *S. coelicolor* is apparent outside of the Bcl-2 domains. However, both Bcl-MT (and its *Mycobacterium* homologs Bcl-MA, Bcl-ML, Bcl-MB and Bcl-MS), and Bcl-SC have similar structural features in that they contain four transmembrane helices at the N-terminus. Therefore, the native *Streptomyces* and *Mycobacterium* Bcl-2 domain containing polypeptides are likely to be integral membrane proteins.

By FFAS analysis, the Bcl-2 domains of Bcl-MT and Bcl-SC show highest structural similarity to the Bcl-2 domain of the *Drosophila* protein designated Drob-1 and to the Bcl-2 domain of the chicken protein designated myeloid cell leukemia-1 (MCL-1). Drob-1 is considered to be mostly pro-apoptotic, but has been suggested to be anti-apoptotic in certain contexts. MCL-1 is considered to be anti-apoptotic, but a splice variant is pro-apoptotic.

Also provided are isolated nucleic acid molecules encoding modifications of the bacterial Bcl-2 domains designated SEQ ID NOS:5, 9, 13, 17, 21 and 25. The term "modification" refers to an amino acid sequence having substantial identity, such as at least about 50% identity, with respect to the reference amino acid sequence, and retaining comparable biological activity characteristic of the polypeptide defined by the reference amino acid sequence. Polypeptides that are "modifications" can have at least about 50%, 60%, 70%, 80%, 85%, 90%, 92%, 95%, 98% or greater amino acid sequence identity with respect to the reference sequence, while retaining comparable biological activity.

Identity of any two nucleic acid or amino acid sequences can be determined by those skilled in the art based, for example, on a BLAST 2.0 computer alignment. BLAST 2.0 searching is known in the art and is publicly available, for example, at http://worldwideweb.ncbi.nlm.nih.gov/BLAST/, as described by Tatusova et al., *FEMS Microbiol Lett.* 174: 247-250 (1999).

Based on the identification of Bcl-2 domain-containing polypeptides in members of both the *Mycobacterium* genus and the *Streptomyces* genus, it is contemplated that Bcl-2 domain-containing polypeptides are widely expressed in prokaryotes. Methods to identify bacterial Bcl-2 domain-encoding nucleic acid molecules and encoded polypeptides that have substantial identity to the reference sequences include analysis of microbial DNA databases to identify structurally similar molecules, according to the methods disclosed herein (see Example).

Alternative methods to identify bacterial Bcl-2 domain-encoding nucleic acid molecules and encoded polypeptides that have substantial identity to the reference sequences include hybridization-based or antibody-based DNA library screening methods to identify molecules with similar primary sequence. DNA libraries, including expression libraries, from a variety of bacterial and eukaryotic species are commercially available or can be readily prepared, and can be probed with Bcl-2 domain-encoding nucleic acid molecules, amplified using oligonucleotide primers, or contacted with antibodies, according to methods known in the art. From an initially identified fragment, nucleic acid molecules encoding full-length polypeptides can be obtained, if desired, by a variety of methods well-known in the art, such as 5' and 3' RACE.

A polypeptide having substantial identity to a reference bacterial Bcl-2 domain can have, for example, one or more additions, deletions or substitutions compared with the reference amino acid sequence. Such modifications can be advantageous, for example, in enhancing the stability, bioavailability, bioactivity or immunogenicity of the polypeptide, or to facilitate its purification.

Modifications to the recited amino acid sequences can be randomly generated, such as by random insertions, deletions or substitutions of nucleotides in a nucleic acid molecule encoding the polypeptide. Alternatively, modifications can be directed, such as by site-directed mutagenesis of an encoding nucleic acid molecule.

Computer programs known in the art can provide guidance in predicting which amino acid residues can be modified without abolishing the function of the polypeptide. Additionally, guidance in modifying amino acid residues of a Bcl-2 domain containing polypeptide, while retaining function can be provided by structure-function studies of other Bcl-2 domain containing polypeptides. It is well known in the art that evolutionarily conserved amino acid residues and structural motifs are more likely to be important for maintaining biological activity than less well-conserved residues and domains.

Thus, it would be expected that substituting a residue that that is highly conserved among Bcl-2 domain containing polypeptides across microbial species with a non-conserved residue may be deleterious, whereas making the same substitution at a residue which varies widely among species would likely not have a significant effect on biological activity. The skilled person, based on the alignment shown in FIG. 1, and knowledge of the conserved structural features of Bcl-2 domains and amphipatic helices therefrom, could predict the effect of any modification and confirm its effect by the methods described herein.

Substitutions to a recited amino acid sequence can either be conservative or non-conservative. Conservative amino acid substitutions include, but are not limited to, substitution of an apolar amino acid with another apolar amino acid (such as replacement of leucine with an isoleucine, valine, alanine, proline, tryptophan, phenylalanine or methionine); substitution of a charged amino acid with a similarly charged amino acid (such as replacement of a glutamic acid with an aspartic acid, or replacement of an arginine with a lysine or histidine); substitution of an uncharged polar amino acid with another uncharged polar amino acid (such as replacement of a serine with a glycine, threonine, tyrosine, cysteine, asparagine or glutamine); or substitution of a residue with a different functional group with a residue of similar size and shape (such as replacement of a serine with an alanine; an arginine with a methionine; or a tyrosine with a phenylalanine).

Additions to a recited amino acid sequence designated include, but are not limited to, the addition of "tag" sequences, such as epitope tags, histidine tags and glutathione-S-transferase (GST), and the like, as well as localization sequences (e.g. membrane localization sequences) and sorting sequences. Such additional sequences can be used, for example, to facilitate expression, purification or characterization of a recombinant polypeptide or to direct the localization of the polypeptide to a desired cellular location.

An exemplary modification of a Bcl-2 domain-containing polypeptide is fusion of the Bcl-2 domain or functional fragment thereof with a heterologous membrane anchor sequence, such as the hydrophobic tail of Bak (amino acids 187-211; Chittendon et al., *EMBO J.* 14:5589-5596 (1995)). Such a construct can ensure appropriate subcellular localization of the Bcl-2 domain for activity.

Deletions to a recited amino acid sequence include, but are not limited to, deletion of residues at the N- and C-termini, or between conserved helices, that are not critical for function.

Biological activities of an invention Bcl-2 domain-containing polypeptide or functional fragment include, for example, pro-apoptotic activity, anti-apoptotic activity, and association with polypeptides in the apoptotic pathway. These and other biological activities of eukaryotic and viral Bcl-2 domain-containing polypeptides are well known in the art (see, for example, Hengartner, *Nature* 407:770-776 (2000)) and are proposed to be similar for the invention bacterial Bcl-2 domain-containing polypeptides.

Pro-apoptotic and anti-apoptotic biological activities of an invention Bcl-2 domain-containing polypeptide can be evidenced in the bacteria itself or in infected host cells. Pro-apoptotic and anti-apoptotic activities refer to an increased or decreased amount of apoptosis, respectively, which can be manifested under normal conditions; under conditions in which other apoptotic molecules (such as adaptor proteins, caspases, cytokine receptors, other Bcl-2 family members, and the like) are over-expressed, deleted or mutated; under conditions in which apoptotic inducers, such as chemotherapeutic or anti-infective agents, have been applied; or under conditions of environmental stress, such as oxidative stress, nutrient deprivation, heat shock and the like.

Methods of detecting apoptotic activities in vivo and in cell-free systems are well known in the art (see, for example, Reed, ed., *Meth. Enz.* Vol. 322 (2000), particularly Chapters 1-5 and 15-17). For example, DNA fragmentation is characteristic of apoptosis, and kits for detecting DNA fragmentation, such as the Apoptag™ detection kit (Intergen, Purchase, N.Y.), are commercially available. Alternatively, pulsed-field gel electrophoresis and conventional agarose gel electrophoresis can be used to detect DNA fragmentation.

An alternative method of detecting apoptotic activity is to detect caspase activation, which only occurs during apoptosis. For example, Su et al., *Exp. Neurol.* 163:9-19 (2000) describes detecting a cleavage product of an endogenous caspase substrate using CM1 antibody (IDUN Pharmaceuticals, La Jolla, Calif.) to detect the p18 subunit of processed, active caspase-3. Caspase activation can also be determined using an exogenous substrate. For example, Haraguchi et al., *J. Exp. Med.* 191:1709-1720 (2000) describes detecting caspase activation using various commercially available fluorigenic substrate peptides, and monitoring release of the fluorigenic moiety from the substrate peptide using a fluorimeter plate reader.

A further method of detecting apoptotic activity is based on the observation that an early event in apoptosis is translocation of phosphatidylserine (PS) to the outer surface of the plasma membrane. Annexin V has been shown to specifically bind PS. Accordingly, such an assay can employ annexin V-FITC/propidium iodide staining and two-color FACS analysis. Apoptotic cells can be characterized as annexin V positive, but propidium iodide negative (Haraguchi et al., *supra* (2000)).

Another method of detecting apoptotic activity is based on the observation that loss of mitochondrial membrane potential occurs as an early event in apoptosis. A change in mitochondrial membrane potential can be detected using a potential-sensitive dye, such as rh123, carbocyanine $DiOC_6$, TREM and the like (Haraguchi et al., *supra* (2000)). Cells at early stages of apoptosis can be distinguished from necrotic cells or late apoptotic cells with impaired membrane integrity in this method using propidium iodide staining.

A further method of detecting apoptotic activity is to directly determine modulation of cell death and survival. For example, recombinant expression of Bax in *S. cerevisiae* induces apoptotic cell death. The lethal effect of Bax can be reverted by co-expression of anti-apoptotic Bcl-2 family members. Therefore, reversion of the lethal effect of overexpressed Bax (or other pro-apoptotic protein) in yeast (or other convenient cell type) is indicative of anti-apoptotic activity (see Xu et al., Meth. Enz. 322:283-296 (2000)).

Other methods of detecting apoptosis suitable for a particular application can be determined by those skilled in the art.

Biological activities of Bcl-2 domain-containing polypeptides also include association with other bacterial polypeptides or with polypeptides in an infected host cell. For example, heterodimerization of an invention polypeptide with a host cell or bacterial pro- or anti-apoptotic Bcl-2 family member (such as Bcl-2, Bcl-$X_L$, A1, Boo, Bcl-w, Bcl-B, Mcl-1, Bax, Bak, Bok, Bim, Bik, Bad, Bid, Hrk, Noxa and the like) can sequester the associated protein and inhibit its pro- or anti-apoptotic activity; homo-oligomerization of an invention polypeptide can result in the formation of a pore through which cytochrome c and other intermembrane proteins can escape, or result in the formation a weakly selective ion channel; association of an invention polypeptide with adaptor molecules, such as BAR, Bap31, Aven or Apaf1, can regulate the caspase cascade; and association with mitochondrial proteins such as the voltage-dependent anion channel (VDAC) or the adenosine nucleotide transporter (ANT) can either generate a pore for cytochrome c exit or modulate mitochondrial homeostasis. Methods for detecting polypeptide-polypeptide associations are well known in the art, and are described further below.

The invention also provides isolated nucleic acid molecules encoding functional fragments of the Bcl-2 domain-containing polypeptides described above. As used herein, the term "functional fragment" refers to a polypeptide exhibiting at least one biological activity of the Bcl-2 domain-containing polypeptide. In one embodiment, the functional fragment contains the amino acid sequence of a BH3 domain from Bcl-MT, Bcl-MA, Bcl-ML, Bcl-MB, Bcl-MS or Bcl-SC, as indicated by the overlined sequences shown on FIG. 1 (amino acids 201-216 of SEQ ID NO:2; amino acids 319-334 of SEQ ID NO:7; amino acids 159-171of SEQ ID NO:11; amino acids 217-232 of SEQ ID NO:15; amino acids 209-224 of SEQ ID NO:19; amino acids 230-245 of SEQ ID NO: 23).

The skilled person will appreciate that the boundaries of a BH3 domain from Bcl-MT, Bcl-MA, Bcl-ML, Bcl-MB, Bcl-MS or Bcl-SC can differ from the exact regions indicated above by virtue of a shift N-terminally or C-terminally of several amino acids, such as 1, 2, 3 or more amino acids, relative to the indicated sequence. Generally, a BH3 domain will contain about 15 amino acids, but can also contain less or more than the recited 15 amino acids, such as 10, 11, 12, 13, 14, 16, 17, 18, 19 or 20 amino acids, and still retain the function of a BH3 domain.

In another embodiment, the functional fragment contains the amino acid sequence of a BH1 motif from Bcl-MT, Bcl-MA, Bcl-ML, Bcl-MB, Bcl-MS or Bcl-SC. The BH1 motif overlaps with helix 5, as shown in FIG. 1. The skilled person will appreciate that the boundaries of a BH1 domain from Bcl-MT, Bcl-MA, Bcl-ML, Bcl-MB, Bcl-MS or Bcl-SC can differ from the exact regions indicated in FIG. 1 by virtue of a shift N-terminally or C-terminally of several amino acids, such as 1, 2, 3, 4, 5 or more amino acids, relative to the indicated sequence. Generally, a BH1 domain will contain about 15 amino acids, but can also contain less or more than 15 amino acids, such as 10, 11, 12, 13, 14, 16, 17, 18, 19 or 20 amino acids, and still retain the function of a BH1 domain.

Because of the importance of the BH3 and BH1 regions in heterodimerization, fragments containing either the BH3 or BH1 regions, or both regions, can retain one or more of the biological activities of the full-length protein, thereby heterodimerizing with other Bcl-2 family members in an infected host cell, or competing with the native bacterial Bcl-2 domain or full-length polypeptide for heterodimerizing with other Bcl-2 family members.

For example, as described in Holinger et al., *J. Biol. Chem.* 274:13298-13304 (1999), synthetic 15-amino acid BH3 peptides from Bak are biologically active and able to bind to Bcl-$x_L$ and induce apoptosis. In that study, the Bak BH3 peptides were introduced into cells either by microinjection or delivered as fusions with Antennapedia internalization sequences. Likewise, as described in Cosulich et al., *Curr. Biol.* 7:913-920 (1997), the BH3 domain of the pro-apoptotic proteins Bax and Bak bind to Bcl-2 and are sufficient to trigger cytochrome c release, caspase activation and apoptosis. In that study, the BH3 peptides were recombinantly expressed as GST fusions, and added to a cell-free *Xenopus* egg extract system that reproduces the morphological and biochemical events characteristic of apoptosis was used.

As further indication that short fragments of Bcl-2 domain-containing proteins are functional, Shimizu et al., *Proc. Natl. Acad. Sci. USA* 97:3100-3105 (2000) described the ability of synthetic BH4 peptides from Bcl-$X_L$ to inhibit voltage-dependent anion channel activity and, when fused to the protein transduction domain of HIV TAT, to prevent apoptotic cell death.

Therefore, it is expected that a functional fragment of a Bcl-2 polypeptide described herein would also retain a biological activity of the full-length protein, and thus also be able to bind a cellular polypeptide and/or to modulate apoptosis either alone or as a fusion protein.

Further provided are isolated oligonucleotides containing at least 17 contiguous nucleotides of a Bcl-2 domain-encoding nucleic acid molecule or of its complement. An isolated oligonucleotide can thus contain at least 18, 19, 20, 22, or at least 25 contiguous nucleotides, such as at least 30, 40, 50, 60, 70, 80, 90, 100, 125, 150, 175, 200, 225, 250, 275, 300, 350, 400, 500, 600, 700, 800 or more contiguous nucleotides from the reference nucleotide sequence, up to the full length sequence. An invention oligonucleotide can be single or double stranded, and represent the sense or antisense strand. An invention oligonucleotide can, but need not, encode a functional polypeptide and can, but need not, be inserted into a vector.

In one embodiment, the isolated oligonucleotide comprises at least 17 contiguous nucleotides of SEQ ID NOS:4, 8, 12, 16, 20 or 24, or the complement thereof. Such oligonucleotides are able to specifically hybridize to a bacterial Bcl-2 domain-encoding nucleic acid molecule under highly stringent hybridization conditions. Therefore, the invention oligonucleotides can be advantageously used, for example, as probes to detect bacterial Bcl-2 domain-encoding nucleic acid molecules in a sample; as sequencing or PCR primers; as antisense reagents to block transcription of a Bcl-2 domain-encoding nucleic acid molecule in a bacterial or infected host cell; or in other applications known to those skilled in the art in which hybridization to a Bcl-2 domain-encoding nucleic acid molecule is desirable.

Specific hybridization refers to the ability of a nucleic acid molecule to hybridize to the reference nucleic acid molecule without hybridization under the same conditions with nucleic acid molecules that are not the reference molecule, such as actin cDNA. Moderately stringent hybridization conditions are conditions equivalent to hybridization of filter-bound nucleic acid in 50% formamide, 5×Denhart's solution, 5×SSPE, 0.2% SDS at 42° C., followed by washing in 0.2×SSPE, 0.2% SDS, at 50°. Highly stringent conditions are conditions equivalent to hybridization of filter-bound nucleic acid in 50% formamide, 5×Denhart's solution, 5×SSPE, 0.2% SDS at 42° C., followed by washing in 0.2×SSPE, 0.2% SDS, at 65° C. Other suitable moderately stringent and highly stringent hybridization buffers and conditions are well known to those of skill in the art and are described, for example, in Sambrook et al., *Molecular Cloning: A Laboratory Manual,* 3rd ed., Cold Spring Harbor Press, Plainview, N.Y. (2001) and in Ausubel et al. (*Current Protocols in Molecular Biology* (Supplement 47), John Wiley & Sons, New York (1999)).

An invention nucleic acid molecule or oligonucleotide containing a Bcl-2 domain-encoding nucleotide sequence can further contain nucleotide additions, which optionally can encode additional polypeptide sequence as described above. Other additional nucleotide sequences include, for example, sequences that facilitate identification or purification of the oligonucleotide, and sequences that facilitate cloning, such as restriction endonuclease recognition sites.

In one embodiment, the invention provides a primer pair containing an isolated oligonucleotide containing at least 17 contiguous nucleotides of a Bcl-2 domain-encoding nucleic acid molecule and an isolated nucleic acid molecule containing at least 17 contiguous nucleotides of the complement of a Bcl-2 domain-encoding nucleic acid molecule. The primer pair can be used, for example, to amplify a Bcl-2 domain-encoding nucleic acid molecule by the polymerase chain reaction (PCR). The skilled person can determine an appropriate primer length and sequence composition for the intended application.

The isolated Bcl-2 domain-encoding nucleic acid molecules and oligonucleotides of the invention can be produced or isolated by methods known in the art. The method chosen will depend, for example, on the type of nucleic acid molecule one intends to isolate. Those skilled in the art, based on knowledge of the nucleotide sequences disclosed herein, can readily isolate Bcl-2 domain-containing nucleic acid molecules as genomic DNA, or regulatory sequences therefrom; as full-length cDNA or desired fragments therefrom; or as full-length mRNA or desired fragments therefrom, by methods known in the art.

An invention Bcl-2 domain-containing polypeptide, functional fragment or peptide does not consist of the exact sequence of the amino acid sequence set forth in publically available databases, or of the exact amino acid sequence of a translated product of a nucleic acid molecule set forth in publically available databases. Likewise, an invention nucleic acid molecule encoding a Bcl-2 domain-containing polypeptide or functional fragment, or Bcl-2 domain oligonucleotide, does not consist of the exact sequence of a nucleotide sequence set forth in publically available databases, such as Expressed Sequence Tags (ESTs), Sequence Tagged Sites (STSs) and genomic fragments, deposited in public databases such as the nr, dbest, dbsts and gss databases, and TIGR, SANGER center, WUST1 and DOE databases of microbial genomes.

In some embodiments, specifically excluded from the invention polypeptides and nucleic acid molecules are the *M. tuberculosis* amino acid sequences designated SEQ ID NO:2 (GenBank Accession gi:7477511; gi:2827576) and SEQ ID NO:3 (GenBank Accession gi:13883066; predicted protein Rv3166c from gi:4160309), and the encoding nucleotide sequence designated SEQ ID NO:1; the *M. avium* amino acid sequence designated SEQ ID NO:7, and its encoding nucleotide sequence designated SEQ ID NO:6; the *M. leprae* amino acid sequence designated SEQ ID NO:11, and its encoding nucleotide sequence designated SEQ ID; the *M. bovis* amino acid sequence designated SEQ ID NO:15, and its encoding nucleotide sequence designated SEQ ID NO:14; the *M. smegmatis* amino acid sequence designated SEQ ID NO:19, and its encoding nucleotide sequence designated SEQ ID NO:18; the *S. coelicolor* amino acid sequence designated SEQ ID NO:23 (GenBank Accession gi:7481597), and its encoding nucleotide sequence designated SEQ ID NO:22. Further excluded are sequences present in compilations of genomic sequencing projects, including GenBank Accession numbers gi:3242278 and gi:4160309.

Since one of skill in the art will realize that the above-recited excluded sequences may be revised at a later date, it is intended that the above-recited sequences are excluded as they stand on the priority date of this application.

One useful method for producing an isolated Bcl-2 domain-encoding nucleic acid molecule of the invention involves amplification of the nucleic acid molecule using the polymerase chain reaction (PCR) and specific primers and, optionally, purification of the resulting product by gel electrophoresis. Either PCR or reverse-transcription PCR (RT-PCR) can be used to produce a nucleic acid molecule having any desired nucleotide boundaries. Desired modifications to the nucleic acid sequence can also be introduced by choosing an appropriate primer with one or more additions, deletions or substitutions. Such nucleic acid molecules can be amplified exponentially starting from as little as a single gene or mRNA copy, from any cell, tissue or species of interest.

Furthermore, isolated Bcl-2 domain-encoding nucleic acid molecules and oligonucleotides of the invention can be produced by synthetic means. For example, a single strand of a nucleic acid molecule can be chemically synthesized in one piece, or in several pieces, by automated synthesis methods known in the art. The complementary strand can likewise be synthesized in one or more pieces, and a double-stranded molecule made by annealing the complementary strands. Direct synthesis is particularly advantageous for producing relatively short molecules, such as oligonucleotide probes and primers, and nucleic acid molecules containing modified nucleotides or linkages.

The invention also provides a vector containing an isolated nucleic acid molecule encoding a Bcl-2 domain-containing polypeptide. The vectors of the invention are useful, for example, for subcloning and amplifying a Bcl-2 domain-encoding nucleic acid molecule, and for recombinantly expressing a Bcl-2 domain-containing polypeptide. A vector of the invention can include a variety of elements useful for cloning and/or expression of the encoded nucleic acid molecule, such as enhancer sequences and promoter sequences from a viral, bacterial or mammalian gene, which provide for constitutive, inducible or cell-specific RNA transcription; transcription termination and RNA processing signals, including polyadenylation signals, which provide for stability of a transcribed mRNA sequence; an origin of replication, which allows for proper episomal replication; selectable marker genes, such as a neomycin or hygromycin resistance gene, useful for selecting stable or transient transfectants in mammalian cells, or an ampicillin resistance gene, useful for selecting transformants in prokaryotic cells; and versatile multiple cloning sites for inserting nucleic acid molecules of interest.

Cloning vectors of the invention include, for example, viral vectors such as a bacteriophage, a baculovirus or a retrovirus; cosmids or plasmids; and, particularly for cloning large nucleic acid molecules, bacterial artificial chromosome vectors (BACs) and yeast artificial chromosome vectors (YACs). Such vectors are commercially available, and their uses are well known in the art.

If it is desired to express RNA transcripts or polypeptides, the invention nucleic acid molecule can be inserted into an expression vector such that it is operatively linked to a promoter of RNA transcription. The term "operatively linked," as used herein, is intended to mean that the nucleic acid molecule is positioned with respect to the endogenous promoter, or heterologous promoter, in such a manner that the promoter will direct the transcription of RNA using the nucleic acid molecule as a template. Methods for operatively linking a nucleic acid to a desired promoter are well known in the art and include, for example, cloning the nucleic acid into a vector containing the desired promoter, or appending the promoter to a nucleic acid sequence using PCR. Thus, an expression vector containing an invention nucleic acid molecule operatively linked to a promoter of RNA transcription can be used to express Bcl-2 domain transcripts and polypeptides in a desired host cell, or in an in vitro system, such as an extract or lysate that supports transcription and translation. Contemplated expression vectors include vectors containing regulatory sequences known in the art to provide for expression in bacterial cells, yeast cells, insect cells, amphibian cells, mammalian cells (including human, non-human primate and rodent cells) and other vertebrate cells.

A variety of expression vectors are commercially available, and can be further modified, if desired, to include appropriate regulatory elements to provide for the desired level of expression or replication in the host cell. For example, appropriate promoter and enhancer elements can be chosen to provide for constitutive, inducible or cell type-specific expression. Useful constitutive promoter and enhancer elements for expression of polypeptides in mammalian cells include, for example, RSV, CMV, SV40 and IgH elements. An exemplary inducible expression element is a steroid response element, while an exemplary cell-specific expression element is a prostate specific antigen (PSA) regulatory sequence. Other constitutive, inducible and cell type-specific regulatory elements are well known in the art.

Exemplary host cells that can be used to express recombinant molecules include mammalian primary cells; established mammalian cell lines, such as COS, CHO, HeLa, NIH3T3, HEK 293-T and PC12 cells; amphibian cells, such as Xenopus embryos and oocytes; and other vertebrate cells. Exemplary host cells also include insect cells (e.g. Drosophila), yeast cells (e.g. *S. cerevisiae, S. pombe,* or *Pichia pastoris*) and prokaryotic cells (e.g. *E. coli*).

Methods for introducing a cloning or expression vector into a host cell are well known in the art and include, for example, various methods of transfection such as calcium phosphate, DEAE-dextran and lipofection methods, viral transduction, electroporation and microinjection. Host cells expressing invention nucleic acid molecules can be used, for example, as a source to isolate recombinantly expressed Bcl-2 domain-containing polypeptides, to identify and isolate molecules that regulate or interact with Bcl-2 domain-containing nucleic acids and polypeptides, or to screen for compounds that enhance or inhibit the activity of a Bcl-2 domain-containing polypeptide, as described further below.

The presence of a bacterial Bcl-2 domain-containing molecule in a sample indicates the presence of the corresponding bacterium, and can also be indicative of the pathogenicity of the bacterium or the stage of infection. Thus, the invention provides methods for detecting a nucleic acid molecule encoding a bacterial Bcl-2 domain-containing polypeptide in a sample. This information can be useful, for example, to diagnose an infection, to determine the nature of the infectious microorganism, and for prognosis of the infection.

In one embodiment, the method is practiced by contacting a sample containing nucleic acids with one or more oligonucleotides containing contiguous sequences from a bacterial Bcl-2 domain-encoding nucleic acid molecule, under high stringency hybridization conditions, and detecting a nucleic acid molecule that hybridizes to the oligonucleotide. In an alternative embodiment the method is practiced by contacting a sample with a primer pair suitable for amplifying a bacterial Bcl-2 domain-encoding nucleic acid molecule, amplifying a nucleic acid molecule using polymerase chain reaction, and detecting the amplification.

As used herein, the term "sample" is intended to mean any biological fluid, cell, tissue, organ or portion thereof, or any environmental sample (e.g. soil, food, water, effluent and the like) that contains or potentially contains bacterial Bcl-2 domain nucleic acid molecules or polypeptides. For example, a sample can be a histologic section of a specimen obtained by biopsy, or cells that are placed in or adapted to tissue culture. A sample further can be a subcellular fraction or extract, or a crude or substantially pure nucleic acid or protein preparation. A sample can be prepared by methods known in the art suitable for the particular format of the detection method employed.

The methods of detecting a Bcl-2 domain-encoding nucleic acid molecule in a sample can be either qualitative or quantitative, and can detect the presence, abundance, integrity or structure of the nucleic acid molecule as desired for a particular application. Suitable hybridization-based assay methods include, for example, in situ hybridization, which can be used to detect altered chromosomal location of the nucleic acid molecule, altered gene copy number, and RNA abundance, depending on the assay format used. Other hybridization methods include, for example, Northern blots and RNase protection assays, which can be used to determine the abundance and integrity of different RNA splice variants, and Southern blots, which can be used to determine the copy number and integrity of DNA. A hybridization probe can be labeled with any suitable detectable moiety, such as a radioisotope, fluorochrome, chemiluminescent marker, biotin, or other detectable moiety known in the art that is detectable by analytical methods.

Suitable amplification-based detection methods are also well known in the art, and include, for example, qualitative or quantitative polymerase chain reaction (PCR); reverse-transcription PCR (RT-PCR); single strand conformational polymorphism (SSCP) analysis, which can readily identify a single point mutation in DNA based on differences in the secondary structure of single-strand DNA that produce an altered electrophoretic mobility upon non-denaturing gel electrophoresis; and coupled PCR, transcription and translation assays, such as a protein truncation test, in which a mutation in DNA is determined by an altered protein product on an electrophoresis gel. The amplified nucleic acid molecule can be sequenced to detect mutations and mutational hot-spots, and specific PCR-based assays for large-scale screening of samples to identify such mutations can be developed.

The invention also provides isolated polypeptides containing bacterial Bcl-2 domains, and functional fragments therefrom, as described above with respect to polypeptides encoded by invention nucleic acid molecules. The invention polypeptides and functional fragments can be introduced into cells (either directly or by recombinant methods) to compete with the native bacterial polypeptide for binding to a host polypeptide, thereby modulating host cell apoptosis and preventing or ameliorating an infection. The invention polypeptides and functional fragments can also be used in screening assays to identify polypeptides and modulatory compounds that bind to and/or alter the activity of the Bcl-2 domain-containing polypeptides. Additionally, the invention polypeptides and functional fragments can be used to raise antibodies, which can be used in diagnostic and prognostic assays.

In one embodiment, the invention provides polypeptides containing Bcl-2 domains from *Mycobacterium* species and *Streptomyces* species, including polypeptides containing the same amino acid sequence as the bacterial Bcl-2 domains from Bcl-MT, Bcl-MA, Bcl-MT, Bcl-MB, Bcl-MS and Bcl-SC designated SEQ ID NOS:5, 9, 13, 17, 21 or 25, respectively, or a modification thereof.

The invention also provides functional fragments of these molecules, including fragments containing the amino acid sequence of a BH3 helix from Bcl-MT, Bcl-MA, Bcl-ML, Bcl-MB, Bcl-MS or Bcl-SC (see FIG. 1), or containing the amino acid sequence of a BH1 motif from Bcl-MT, Bcl-MA, Bcl-ML, Bcl-MB, Bcl-MS or Bcl-SC (see FIG. 1).

A polypeptide of the invention can contain amino acids with various chemical or enzymatic modifications with respect to naturally occurring amino acids. Such modifications can enhance the stability, bioactivity, immunogenicity or other advantageous property of an invention polypeptide. Thus, a polypeptide can contain an amino acid modified by replacement of hydrogen by an alkyl, acyl, or amino group; by esterification of a carboxyl group with a suitable alkyl or aryl moiety; by alkylation of a hydroxyl group to form an ether derivative; by phosphorylation or dephosphorylation of a serine, threonine or tyrosine residue; by N- or O-linked glycosylation; by iodination; by radiolabeling; or the like. A polypeptide can also include a modified amino acids such as hydroxyproline or carboxyglutamate, or a D-amino acid in place of its corresponding L-amino acid. Those skilled in the art can determine an appropriate amino acid modification for a given application.

In yet another embodiment, the invention provides an isolated Bcl-2 domain peptide containing at least 8 contiguous amino acids of a bacterial Bcl-2 domain-containing polypeptide, such as at least 8 contiguous amino acids of SEQ ID NOS:5, 9, 13, 17, 21 or 25. Such a peptide can contain, for example, at least about 10, 12, 15, 20, 25, 30, 35, 40, 50, 60, 70, 80, 90, 100, 110, 125, 150, 200, 250, 300 or more amino acids, up to the full-length of the reference polypeptide. A peptide of at least about 8 amino acids can be used, for example, as an immunogen to raise antibodies specific for bacterial Bcl-2 domain containing polypeptides, or as an antigen to purify antibodies directed against Bcl-2 domain containing polypeptides. When used as an antigen, an invention peptide can be attached to a carrier molecule such as bovine serum albumin (BSA) or keyhole limpet hemocyanin (KLH).

Peptides that are likely to be antigenic or immunogenic can be predicted using methods and algorithms known in the art and described, for example, by Irnaten et al., *Protein Eng.* 11:949-955 (1998), and Savoie et al., *Pac. Symp. Biocomput.* 1999:182-189 (1999). Immunogenicity of the peptides of the invention can be determined by methods known in the art, such as assay of a delayed-type hypersensitivity response in an animal sensitized to a Bcl-2 domain-containing polypeptide, or by elicitation of antibodies specific for Bcl-2 domain-containing polypeptides. Likewise, antigenicity of the peptides of the invention can be determined by methods known in the art, such as by ELISA analysis, as described, for example, in Harlow and Lane, *Antibodies: A Laboratory Manual,* Cold Spring Harbor Laboratory Press (1988).

The isolated Bcl-2 domain-containing polypeptides, functional fragments and peptides of the invention can be prepared by methods known in the art, including biochemical, recombinant and synthetic methods. For example, polypeptides can be purified by routine biochemical methods from bacteria that express the polypeptide. The detection methods disclosed herein can be adapted for determining which bacteria are appropriate starting materials. Biochemical purification can include, for example, steps such as solubilization of the appropriate cells, size or affinity chromatography, electrophoresis, and immunoaffinity procedures. The methods and conditions for biochemical purification of a polypeptide of the invention can be chosen by those skilled in the art, and purification monitored, for example, by an ELISA assay or a functional assay.

A Bcl-2 domain-containing polypeptide, functional fragment or peptide having any desired boundaries can also be produced by recombinant methods. Recombinant methods involve expressing a nucleic acid molecule encoding the desired polypeptide or fragment in a host cell or cell extract, and isolating the recombinant polypeptide or fragment, such as by routine biochemical purification methods described above. To facilitate identification and purification of the recombinant polypeptide, it is often desirable to insert or add, in-frame with the coding sequence, nucleic acid sequences that encode epitope tags, polyhistidine tags, glutathione-S-transferase (GST) domains, and similar affinity binding sequences. Methods for producing and expressing recombinant polypeptides in vitro and in prokaryotic and eukaryotic host cells are well known in the art.

Thus, the invention provides a method of isolating a Bcl-2 domain-containing polypeptide, by growing a host cell containing an expression vector encoding a Bcl-2 domain-containing polypeptide, under conditions appropriate for expression of the encoded polypeptide, and isolating the encoded polypeptide. In one embodiment, the Bcl-2 domain-containing polypeptide contains an amino acid sequence designated SEQ ID NO:5, 9, 13, 17, 21 or 25, or is a modification thereof.

The invention polypeptide fragments and peptides can also be produced, for example, by enzymatic or chemical cleavage of the full-length polypeptide. Methods for enzymatic and chemical cleavage and for purification of the resultant peptide fragments are well known in the art (see, for example, Deutscher, *Methods in Enzymology,* Vol. 182, "Guide to Protein Purification," San Diego: Academic Press, Inc. (1990)).

The invention also provides an antibody or antigen binding fragment thereof which specifically binds to a Bcl-2 domain-containing polypeptide. Such antibodies, which include polyclonal, monoclonal, chimeric, bifunctional, and humanized antibodies, can be used, for example, to affinity purify a Bcl-2 domain-containing polypeptide from a cell, or in therapeutic and diagnostic applications described below.

An "antigen binding fragment" of an antibody of the invention includes, for example, individual heavy or light chains and fragments thereof, such as VL, VH and Fd; monovalent fragments, such as Fv, Fab, and Fab'; bivalent fragments such as $F(ab')_2$; single chain Fv (scFv); and Fc fragments. Antigen binding fragments include, for example, fragments produced by protease digestion or reduction of an antibody, as well as fragments produced by recombinant DNA methods known to those skilled in the art.

In one embodiment, the invention provides antibodies and antigen binding fragments thereof that specifically bind a Bcl-2 domain-containing polypeptide containing an amino acid sequence designated SEQ ID NOS:5, 9, 13, 17, 21 or 25.

The antibodies of the invention can be produced by any method known in the art. For example, a Bcl-2 domain containing polypeptide or immunogenic peptide of the invention, or a nucleic acid expressing such a polypeptide, can be administered to an animal, using standard methods, and polyclonal antibodies isolated therefrom. Such polypeptides or peptides, if desired, can be conjugated to a carrier, such as KLH, serum albumin, tetanus toxoid and the like, using standard linking techniques, to increase their immunogenicity. Additionally, such peptides can be formulated together with an adjuvant known in the art, such as Freund's complete or incomplete adjuvant. The antibodies so generated can be used in the form of serum isolated from an immunized animal, or the antibody can be affinity purified from the serum using the invention peptides or polypeptides.

Additionally, the antibodies of the invention can be monoclonal antibodies produced by a hybridoma cell line, by chemical synthesis, or by recombinant methods. Modified antibodies, such as chimeric antibodies, humanized antibodies and CDR-grafted or bifunctional antibodies, can also be produced by methods well known to those skilled in the art.

Methods of preparing and using antibodies and antigen-binding fragments, including detectably labeled antibodies, are described, for example, in Harlow and Lane, *Antibodies: A Laboratory Manual,* Cold Spring Harbor Laboratory, New York (1989); in Day, E. D., *Advanced Immunochemistry,* Second Ed., Wiley-Liss, Inc., New York, N.Y. (1990); and in Borrebaeck (Ed.), *Antibody Engineering,* Second Ed., Oxford University Press, New York (1995).

The invention also provides a method for detecting the presence of a polypeptide containing a bacterial Bcl-2 domain in a sample. The method is practiced by contacting a sample with an antibody specific for a bacterial Bcl-2 domain and detecting the presence of specific binding of the antibody to the sample, thereby detecting the presence of a polypeptide containing a Bcl-2 domain in the sample. This information can be useful, for example, to diagnose an infection, to determine the nature of the infectious microorganism, and for prognosis, as described previously with respect to nucleic acid detection methods.

The invention also provides various methods of identifying polypeptides and compounds that modulate the activity of a Bcl-2 domain-containing polypeptide. In embodiments of the methods described herein, polypeptides and compounds that modulate the activity of a Bcl-2 domain-containing polypeptide having the amino acid sequence designated SEQ ID NO:5, 9, 13, 17, 21 or 25 are provided. The term "modulate the activity" means that the Bcl-2 domain modulatory compound (B2MC) either positively or negatively affects a biological activity of a Bcl-2 domain-containing polypeptide. As described above, biological activities of Bcl-2 containing polypeptides include pro- and anti-apoptotic activities, self-association and association with cellular molecules that regulate apoptosis. The identified polypeptides and compounds can be used in a variety of therapeutic applications, as described further below, such as to prevent or treat infectious diseases.

In one embodiment, the invention provides a method of identifying a compound that modulates an apoptotic activity of a Bcl-2 domain-associating polypeptide. The method is practiced by contacting a Bcl-2 domain-containing polypeptide with a candidate compound, and determining an apoptotic activity of the Bcl-2 domain-containing polypeptide. As described above, apoptotic activities of a Bcl-2 domain-containing polypeptide, including both pro- and anti-apoptotic activities, can be determined in vitro or in a cell by methods well known in the art, including determining cell survival/death, DNA fragmentation, mitochondrial depolarization, caspase activation, annexin V/propidium iodide double staining, and the like. A compound that modulates, either positively or negatively, any of these indicia of apoptotic activity can be identified.

The invention also provides a method of identifying a Bcl-2 domain-associating polypeptide (a "B2AP"). The method is practiced by contacting a Bcl-2 domain-containing polypeptide with a candidate polypeptide and determining association between the polypeptides. A polypeptide that associates with the Bcl-2 domain-containing polypeptide is identified as a B2AP. As used herein, the term "associate" means that the molecule binds to the Bcl-2 domain-containing polypeptide relatively specifically and, therefore, can form a bound complex either in a cell or in vitro under suitable conditions.

Associations between polypeptides can be determined by methods known in the art. For example, associations with a bacterial Bcl-2 domain-containing polypeptide or functional fragment thereof can be determined using transcription activation assays, affinity binding assays, co-immunoprecipitation assays, and the like. Various association assays are well known in the art and are described, for example, in Sambrook et al., supra (2001) and Ausubel et al., supra (1999). Exemplary B2APs include, for example, the bacterial Bcl-2 domain-containing polypeptides described herein, host cell Bcl-2 family members (e.g. Bcl-2, Bcl-$X_L$, A1, Boo, Bcl-w, Mcl-1, Bax, Bak, Bok, Bim, Bik, Bad, Bid, Hrk, Noxa and the like), adaptor proteins (e.g. BAR, Bap31, Aven, Apaf1 and the like), and mitochondrial proteins such as VDAC and ANT.

Transcription activation assays such as two-hybrid assays are well known in the art. Such assays are based on the modular nature of transcription factors, which consist of functionally separable DNA-binding and trans-activation domains. When expressed as separate proteins, these two domains fail to mediate gene transcription. However, transcription activation activity can be restored if the DNA-binding domain and the trans-activation domain are bridged together due, for example, to the association of two polypeptides. Two-hybrid systems can use various strains of *S. cerevisiae* as host cells for vectors that express the hybrid proteins. However, similar transcription activation assays also can be performed using other yeast cells or mammalian cells. The skilled person can practice the method by fusing an invention Bcl-2 domain containing polypeptide to a suitable DNA-binding domain or to a suitable trans-activation domain, and fusing one or more sequences potentially encoding a B2AP to the other domain, and observing whether transcriptional activation occurs.

Affinity assays are also well known in the art and include, for example, assays in which the polypeptide of interest is fused to a glutathione-S-transferase (GST) protein, or to another tag that allows binding of the fusion to an affinity matrix. Such assays provide a simple, rapid and inexpensive method for identifying and isolating an associated polypeptide. For example, by recombinant expression, GST can be fused to a Bcl-2 domain-containing polypeptide of the invention, and the fusion expressed and purified by binding to an affinity matrix containing immobilized glutathione. A sample containing a candidate B2AP, such as a bacterial or cellular extract or isolated polypeptide, can be passed over an affinity column containing the bound GST/Bcl-2 domain fusion, and a B2AP obtained. In addition, fusion proteins can be used to screen a cDNA expression library, wherein binding of the Bcl-2 domain-containing protein to a clone indicates that the clone contains a cDNA encoding a B2AP.

The invention also provides a method of identifying a Bcl-2 domain-associating compound (a "B2AC"). The method is practiced by contacting a Bcl-2 domain-containing polypeptide with a candidate compound and determining association between the Bcl-2 domain-containing polypeptide and the candidate compound. A compound that associates with the Bcl-2 domain-containing polypeptide is identified as a B2AC.

A candidate compound can be a naturally occurring macromolecule, such as a peptide, nucleic acid, carbohydrate, lipid, or any combination thereof. A candidate compound also can be a partially or completely synthetic derivative, analog or mimetic of such a macromolecule, or a small organic or inorganic molecule prepared partly or completely by combinatorial chemistry methods.

Methods for producing libraries of candidate compounds, including chemical or biological molecules such as simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., *Curr. Opin. Chem. Biol.* 2:422-428 (1998); Tietze et al., *Curr. Biol.*, 2:363-371 (1998); Sofia, *Mol. Divers.* 3:75-94 (1998); Eichler et al., *Med. Res. Rev.* 15:481-496 (1995); and the like. Libraries containing large numbers of natural and synthetic compounds also can be obtained from commercial sources.

A compound that associates with a Bcl-2 domain-containing polypeptide can be identified using a variety of assay formats. A binding assay can use a detectably labeled candidate compound and an unlabeled Bcl-2 domain-containing polypeptide. Alternatively, a binding assay can use an unlabeled candidate compound and a labeled Bcl-2 domain-containing polypeptide. A variety of low- and high-throughput assays known in the art are suitable for detecting specific binding interactions between a Bcl-2 domain-containing polypeptide and a candidate compound. These assays include both solution-based methods and solid phase methods (e.g. molecules bound to plates, chips, affinity columns and the like). Such binding assays are amenable to either manual or high-throughput automated screening of compounds.

Suitable assays for detecting molecular associations include, for example, scintillation proximity assays (SPA) (Alouani, *Methods Mol. Biol.* 138:135-41 (2000)), UV or chemical cross-linking (Fancy, *Curr. Opin. Chem. Biol.* 4:28-33 (2000)), competition binding assays (Yamamura et al., *Methods in Neurotransmitter Receptor Analysis,* Raven Press, New York, 1990), biomolecular interaction analysis (BIA) such as surface plasmon resonance (SPR) (Weinberger et al., *Pharmacogenomics* 1:395-416 (2000)), mass spectrometry (MS) (McLafferty et al., *Science* 284:1289-1290 (1999) and Degterev, et al., *Nature Cell Biology* 3:173-182 (2001)), nuclear magnetic resonance (NMR) (Shuker etal., *Science* 274:1531-1534 (1996), Hajduk et al., *J. Med. Chem.* 42:2315-2317 (1999), and Chen and Shapiro, *Anal. Chem.* 71:669A-675A (1999)), and fluorescence polarization assays (FPA) (Degterev et al., supra, 2001). Other suitable methods to detect molecular associations are well known in the art (see, for example, Reed, ed., *Meth. Enz. Vol.* 322 (2000), particularly Chapters 24 and 25).

The invention also provides a method of identifying an effective agent that alters the association between a B2AP and a Bcl-2 domain-containing polypeptide. The method is practiced by contacting a Bcl-2 domain-containing polypeptide and the B2AP under conditions that allow the polypeptides to associate, with a candidate compound, and determining association of the polypeptides. A compound that alters the association is identified as an effective agent.

As described above, the invention Bcl-2 containing polypeptides can self-associate, and can associate with other bacterial or host cell Bcl-2 family members, adaptor proteins and mitochondrial proteins. Therefore, invention Bcl-2 domain-containing polypeptides are exemplary B2APs, as are bacterial or host cell Bcl-2 family members, adaptor proteins and mitochondrial proteins that associate with invention Bcl-2 domain-containing polypeptides. Compounds that either promote or disrupt self-association or association with a heterologous bacterial or host cells polypeptide can be identified by in vitro and in vivo methods of detecting polypeptide associations described above.

Additionally, a method of identifying an effective agent that alters the association between a B2AP and a Bcl-2 domain-containing polypeptide can be practiced by co-expressing the B2AP and an invention Bcl-2 domain-containing polypeptide in a cell, such as a yeast or mammalian cell, under conditions in which apoptosis is promoted, and identifying compounds that selectively block apoptosis under these conditions.

Methods for identifying molecules that associate with an invention polypeptide generally require comparison to a control. One type of a "control" is a cell or isolated Bcl-2 domain-containing polypeptide preparation that is treated substantially the same as the test cell or polypeptide, except for being exposed to the candidate molecule. The control cell or isolated polypeptide can be treated with a carrier solution or solvent in which the candidate molecule is dissolved or contained, such as an aqueous or organic solution, if desired.

As described herein, bacterial Bcl-2 domain-containing polypeptides can promote or inhibit apoptosis in infected host cells, thereby contributing to the pathogenic effects of the bacteria in the host cells, and can also promote or inhibit apoptosis-like processes in the bacteria itself. Thus, by selectively manipulating the expression or biological activity of the Bcl-2 domain-containing molecules of the invention, biological processes such as apoptosis can be modulated.

The invention provides methods of modulating apoptosis in a cell by modulating the activity of a bacterial Bcl-2 domain-containing polypeptide. In embodiments of the method, apoptosis is modulated by modulating the activity of a Bcl-2 domain-containing polypeptide having the amino acid sequence designated SEQ ID NO:5, 9, 13, 17, 21 or 25. In one embodiment, the method is practiced by increasing or decreasing the level of a Bcl-2 domain-containing polypeptide or functional fragment in a cell. In another embodiment, the method is practiced by increasing or decreasing the level of a B2AP or functional fragment thereof in a cell. A "cell" can be either a bacterial cell, or a normal or diseased host cell, such as a human, animal or plant cell.

The level of a Bcl-2 domain-containing polypeptide or functional fragment in a cell can be increased by introducing an expressible nucleic acid molecule encoding a bacterial Bcl-2 domain-containing polypeptide or functional fragment thereof into the cell, thereby increasing expression of the Bcl-2 domain-containing polypeptide. The Bcl-2 domain-containing polypeptide or functional fragment can have the same activity as the native polypeptide, or can act as in a dominant negative fashion to inhibit the activity of the native polypeptide. The method can be practiced either ex vivo or in vivo in an infected individual.

A nucleic acid molecule encoding a Bcl-2 domain-containing polypeptide or functional fragment can be introduced into a cell using gene transfer technology known in the art. Gene transfer strategies are well known to those skilled in the art, and successful clinical trials of gene therapy are described, for example in Roth et al., *Oncology* 13(10 Suppl 5):148-154 (1999). Gene transfer is generally practiced using expression vectors, such as viral vectors, viral genomes, plasmids, phagemids and the like, but can optionally be practiced with expressible DNA or mRNA encoding the desired polypeptide, without a vector.

Viral based gene transfer systems are advantageous in being able to introduce relatively high levels of a heterologous nucleic acid into a variety of cells, including nondividing cells. Viral vectors that are compatible with a targeted cell are particularly useful for introducing a nucleic acid molecule encoding a Bcl-2 domain-containing polypeptide or functional fragment into a cell. Suitable viral vectors for gene therapy applications are well known in the art, and include, for example, Herpes simplex virus vectors (U.S. Pat. No. 5,501,979), Vaccinia virus vectors (U.S. Pat. No. 5,506,138), Cytomegalovirus vectors (U.S. Pat. No. 5,561,063), Modified Moloney murine leukemia virus vectors (U.S. Pat. No. 5,693,508), adenovirus vectors (U.S. Pat. Nos. 5,700,470 and 5,731,172), adeno-associated virus vectors (U.S. Pat. No. 5,604,090), constitutive and regulatable retrovirus vectors (U.S. Pat. Nos. 4,405,712; 4,650,764 and 5,739,018, 5,646,013, 5,624,820, 5,693,508 and 5,674,703), papilloma virus vectors (U.S. Pat. Nos. 5,674,703 and 5,719,054), and the like.

The targeting specificity of viral vectors can be utilized to target predetermined cell types and introduce a recombinant gene into the infected cell. Thus, the selection of viral vector will depend, in part, on the cell type to be targeted. For example, if neurodegenerative diseases are to be treated, then a vector specific for cells of the neuronal cell lineage can be used. Such viral vectors include, for example, Herpes simplex virus-based vectors. Similarly, if a disease or pathological condition of the hematopoietic system is to be treated, then a viral vector that is specific for blood cells and their precursors, preferably for the specific type of hematopoietic cell, can be used. Such viral vectors include, for example, HIV-based vectors. The skilled person can determine an appropriate vector for a particular indication to be treated.

Vectors such as those described herein also can express specific receptors or ligands, which can modify or alter target specificity through receptor mediated events. Such vectors can be constructed using recombinant DNA techniques or synthetic chemistry procedures. In addition, a viral vector can be made tissue-specific by incorporating a tissue-specific promotor or enhancer into the vector.

Recombinant adenoviruses having general or tissue-specific promoters can be used to deliver an expression construct into a variety of types of tissues and cells, including non-mitotic cells, and to drive cDNA expression in the target cells. Recombinant adeno-associated viruses also are useful and have the added advantage that the recombinant virus can stably integrate into the chromatin of even quiescent non-proliferating cells such as neurons of the central and peripheral nervous systems.

For gene therapy applications, an expression vector can be administered to a subject by various routes. For example, local administration at the site of a pathology can be advantageous because there is no dilution effect and, therefore, the likelihood that a majority of the targeted cells will be contacted with the nucleic acid molecule is increased. In addition, administration can be via intravenous or subcutaneous injection into the subject. Following injection, the viral vectors will circulate until they recognize host cells with the appropriate target specificity for infection. Injection of viral vectors into the spinal fluid also can be an effective mode of administration, for example, in treating a neurodegenerative disease.

Receptor-mediated DNA delivery approaches also can be used to deliver a nucleic acid molecule into cells in a tissue-specific manner using a tissue-specific ligand or an antibody that is non-covalently complexed with the nucleic acid molecule via a bridging molecule. Direct injection of a naked or a nucleic acid molecule encapsulated, for example, in cationic liposomes also can be used for stable gene transfer into non-dividing or dividing cells. In addition, an expressible nucleic acid molecule can be transferred into a variety of tissues using the particle bombardment method.

The level of a bacterial Bcl-2 domain-containing polypeptide in a cell can be decreased, for example, by introducing an antisense nucleic acid molecule, ribozyme or double-stranded RNA interference construct into the cell. For example, an 18-mer all-phosphothioate Bcl-2 antisense oligonucleotide (G3139; Genta) has been used to target the first six codons of the human Bcl-2 open reading frame, successfully precluding its translation. The balance is thus shifted between pro- and anti-apoptotic family members in favor of pro-apoptotic members, resulting in apoptosis. G3139 has also been demonstrated to be effective in enhancing apoptosis in pre-clinical studies in animals as well as in human clinical trials for various cancers.

Likewise, antisense nucleotide sequences that are complementary to the 5'-region of a nucleic acid molecule encoding a bacterial Bcl-2 domain-containing polypeptide can be used to prevent translation. Therefore, the method can be practiced with an antisense nucleic acid molecule complementary to at least a portion of the nucleotide sequence of SEQ ID NOS:1, 6, 10, 14, 18 or 22. For example, the antisense nucleic acid molecule can be complementary to a region within nucleotides 1-100 of SEQ ID NOS:1, 6, 10, 14, 18 or 22, such as nucleotides 1-18 of SEQ ID NOS:1, 6, 10, 14, 18 or 22, and can optionally include sequences determined to be 5' to the start codon. Antisense nucleotide sequences that are complementary to other portions of SEQ ID NOS:1, 6, 10, 14, 18 or 22, including portions of the Bcl-2 domain-encoding sequence (SEQ ID NOS: 4, 8, 12, 16, 20 or 24, respectively) can also be effective.

Methods of preparing antisense nucleic acids molecules and using them therapeutically are known in the art and described, for example, in Galderisi et al., *J. Cell Physiol.* 181:251-257 (1999). Likewise, methods of preparing ribozymes and DNA encoding ribozymes, including hairpin and hammerhead ribozymes, and using them therapeutically are known in the art and described, for example, in Lewin et al., *Trends Mol. Med.* 7:221-228 (2001). Such ribozymes can target and cleave a nucleotide sequence selected from SEQ ID NOS:1, 6, 10, 14, 18 or 22.

RNA interference (RNAi) is a method of sequence-specific gene silencing by post-transcriptional RNA degradation, which is initiated by double-stranded RNA (dsRNA) homologous in sequence to the silenced gene. A suitable double-stranded RNA (dsRNA) for RNAi contains sense and antisense strands of about 21 contiguous nucleotides corresponding to the gene to be targeted that form 19 RNA base pairs, leaving overhangs of two nucleotides at each 3' end (Elbashir et al., *Nature* 411:494-498 (2001); Bass, *Nature* 411:428-429 (2001); Zamore, *Nat. Struct. Biol.* 8:746-750 (2001)). dsRNAs of about 25-30 nucleotides have also been used successfully for RNAi (Karabinos et al., *Proc. Natl. Acad. Sci.* 98:7863-7868 (2001). Optionally, the dsRNA can be a hairpin construct (Svoboda et al., *Biochem. Biophys. Res. Commun.* 287:1099-1104 (2001)). dsRNA can be synthesized in vitro and introduced into a cell by methods known in the art. By such methods, the targeted RNA is degraded, and translation of the target polypeptide is decreased or abolished.

Antisense RNA, ribozymes and dsRNA nucleic acid molecules can be produced in a cell using expression vectors as described above. Alternatively, synthetic nucleic acid molecules can be introduced directly into cells or can be encapsulated in liposomes to facilitate transfer of the nucleic acid molecules into a cell. Where antisense oligonucleotides, ribozymes or dsRNA nucleic acid molecules are directly administered, it can be desirable to construct the nucleic acid molecules using nucleotide analogs or with a peptide nucleic acid backbone, in order to confer increased stability on the molecule in vivo.

Likewise, the levels of a B2AP identified by the methods described herein, or a fragment thereof that associates with an invention Bcl-2 domain-containing polypeptide, can be increased or decreased by gene therapy, antisense, ribozyme or RNAi methods as described above. Such methods can also promote or inhibit apoptosis, either directly or by modulating the activity of the bacterial Bcl-2 domain-containing polypeptide that associates with the B2AP.

In another embodiment, the method of modulating apoptosis in a cell is practiced by contacting the cell with an effective amount of a B2AC, with an effective agent that alters the association between a B2AP and a Bcl-2 domain-containing polypeptide, or a B2MC. Methods of identifying such compounds have been described above.

In yet another embodiment, the method of modulating apoptosis in a cell is practiced by contacting the cell with an effective amount of an antibody specific for a bacterial Bcl-2 domain-containing polypeptide. If desired, such antibodies can be administered in conjunction with a cytotoxic or cytostatic moiety, such as a radioisotope or toxin, in order to neutralize or kill cells expressing a bacterial Bcl-2 domain-containing polypeptide.

The invention further provides a method of preventing or treating a pathologic condition in an individual by administering to the individual a therapeutic molecule described above, such as a nucleic acid molecule that directs the expression of a bacterial Bcl-2 domain-containing polypeptide or functional fragment; an antisense nucleic acid molecule, ribozyme or dsRNA that inhibits expression of bacterial Bcl-2 domain-containing polypeptides; B2ACs; B2MCs; effective agents that alter the association between a B2AP and a Bcl-2 domain-containing polypeptide; and antibodies. Pathologic conditions amenable to such methods are those that are characterized, at least in part, by altered apoptosis, such as infectious diseases, cancer, autoimmune diseases and neurodegenerative diseases and the like. The invention molecules can be used to prevent or treat such conditions in humans and other mammals, including livestock, veterinary animals and research animals.

As described previously, under conditions of environmental stress many bacteria undergo an apoptosis-like process. Additionally, as part of their pathogenic mechanism, many infectious bacteria either promote or inhibit host cell apoptosis. Therapeutic molecules described herein that increase or decrease the levels of apoptosis in the bacteria, or increase or decrease the levels of apoptosis in infected host cells, can be used to decrease bacterial survival and inhibit their pathogenesis. Thus, the molecules of the invention can be used in all applications currently known for antibiotics, including preventing and treating infectious diseases.

Exemplary infectious diseases amenable to prevention or treatment with the therapeutic molecules described herein include tuberculosis and other pulmonary diseases and skin diseases caused by Mycobacterial species. Other infectious diseases caused by bacteria vary depending on the pathogen and are well known in the art.

Therapeutic molecules described herein that increase the levels of apoptosis in a host cell can also be used to treat hyperproliferative conditions, such as cancer, in which it is desired to prevent unregulated cell proliferation. Similarly, such molecules can be used to treat autoimmune diseases, where it is desirable to induce apoptosis in the immunoeffector cells that mediate the disease. Therapeutic molecules described herein that inhibit the level of apoptosis of cells can be used to treat an individual having a disease characterized by a pathologically elevated level of apoptosis, such as occurs in neuronal cells in patients with neurodegenerative diseases, including Parkinson's disease, Huntington's disease, Alzheimer's disease and the encephalopathy that occurs in AIDS patients.

As used herein, the term "treating" a pathological condition is intended to mean any detectable beneficial therapeutic effect on the pathological condition of the individual being treating. The beneficial effect can be evidenced, for example, by a delayed onset of clinical symptoms, a reduction in severity of some or all clinical symptoms of the disease, a slower progression of the disease, a reduction in the number of relapses of the disease, a reduction in the number or activity of pathogenic cells, an improvement in the overall health or well-being of the individual, or by other parameters well known in the art that are specific to the particular condition.

The therapeutic molecules described herein, including expression constructs, antisense nucleic acid molecules, ribozymes, dsRNAs, B2ACs, B2MCs, effective agents, and antibodies, can optionally be formulated together with a pharmaceutically acceptable carrier for delivery to a cultured cell or to an individual. Suitable pharmaceutically acceptable carriers are well known in the art and include, for example, aqueous or organic solvents such as physiologically buffered saline, glycols, glycerol, oils or injectable organic esters. A pharmaceutically acceptable carrier can also contain a physiologically acceptable compound that acts, for example, to stabilize or increase the solubility of a pharmaceutical composition. Such a physiologically acceptable compound can be, for example, a carbohydrate, such as glucose, sucrose or dextrans; an antioxidant, such as ascorbic acid or glutathione; a chelating agent; a low molecular weight protein; or another stabilizer or excipient. Pharmaceutically acceptable carriers, including solvents, stabilizers, solubilizers and preservatives, are well known to those skilled in the art.

Those skilled in the art can formulate the therapeutic molecules to ensure proper distribution in vivo. For example, the blood-brain barrier (BBB) excludes many highly hydrophilic compounds. To ensure that the therapeutic molecules of the invention cross the BBB, if desired, they can be formulated, for example, in liposomes, or chemically derivatized. Methods of ensuring appropriate distribution in vivo can also be provided by rechargeable or biodegradable devices, particularly where gradients of concentrations of drug in a tissue are desired. Various slow release polymeric devices are known in the art for the controlled delivery of drugs, and include both biodegradable and non-degradable polymers and hydrogels. Those skilled in the art understand that the choice of the pharmaceutical formulation and the appropriate preparation of the composition will depend on the intended use and mode of administration.

The therapeutic molecules described herein can be administered to a subject by any effective route. Suitable routes for delivering the therapeutic molecules of the invention include topically, intraocularly, intradermally, parenterally, orally, intranasally, intravenously, intramuscularly, intraspinally, intracerebrally and subcutaneously.

An effective dose of a therapeutic molecule described herein can be predicted, for example, by extrapolation from the concentration required to modulate the biological activity of a Bcl-2 domain containing polypeptide in the in vitro or in vivo binding and apoptotic assays described herein. An effective dose of a molecule of the invention can also be predicted from appropriate animal models for the particular disease. The appropriate dose for treatment of a human subject is dependent on the nature and bioactivity of the particular compound, the desired route of administration, the gender, age and health of the individual, the number of doses and duration of treatment, and the particular condition being treated, and can be determined by the clinician.

The following examples are intended to illustrate but not limit the present invention.

EXAMPLE I

This example shows the identification of bacterial Bcl-2 domain-containing molecules.

Bcl-2 domain-containing bacterial polypeptides were identified using the algorithm and approach described in Li et al., *Bioinformatics* 16:1105-1110 (2000). Briefly, a representative set of Bcl-2 domains was used as queries and a cascade of TBLASTN and PSI-BLAST searches was performed on nucleotide databases at NCBI (htgs, gss, dbest) and the NR protein database. Candidate Bcl-2 domain-containing polypeptides were identified in *M. tuberculosis* and *S. coelicolor*.

The candidate Bcl-2 domain-containing polypeptides were confirmed by running a Fold & Function Assignment System (FFAS) fold prediction calculation (Rychlewski et al., *Protein Sci.* 9:232-241 (2000); hypertexttransferprotocol://bioinformatics.ljcrf.edu/FFAS_apoptosis) against a database of proteins of known structures (PDB) enriched in apoptotic domains.

The identified Bcl-2 domain-containing polypeptides were compared against known sequences using a PSI-BLAST search against the NR protein database at NCBI and a FFAS search against the PFAM and COG databases, as well as by Hidden Markov Model (HMM) searches in the PFAM database (pfam.wust1.edu; http://worldwideweb.sanger.ac.uk/Pfam/help/; Bateman et al., *Nucleic Acids Res.* 27:260-262 (1999)).

The Bcl-2 domain was also identified in several nucleotide fragments from related *Mycobacterium* species (*M. avium, M. leprae, M. bovis* and *M. smegmatis*) using TBLASTN searches in the nucleotide databases at NCBI: (unfinished microbial genomes).

EXAMPLE II

This example shows the association between a bacterial Bcl-2 domain-containing polypeptide and mammalian Bcl-2 family members.

Figure 2:
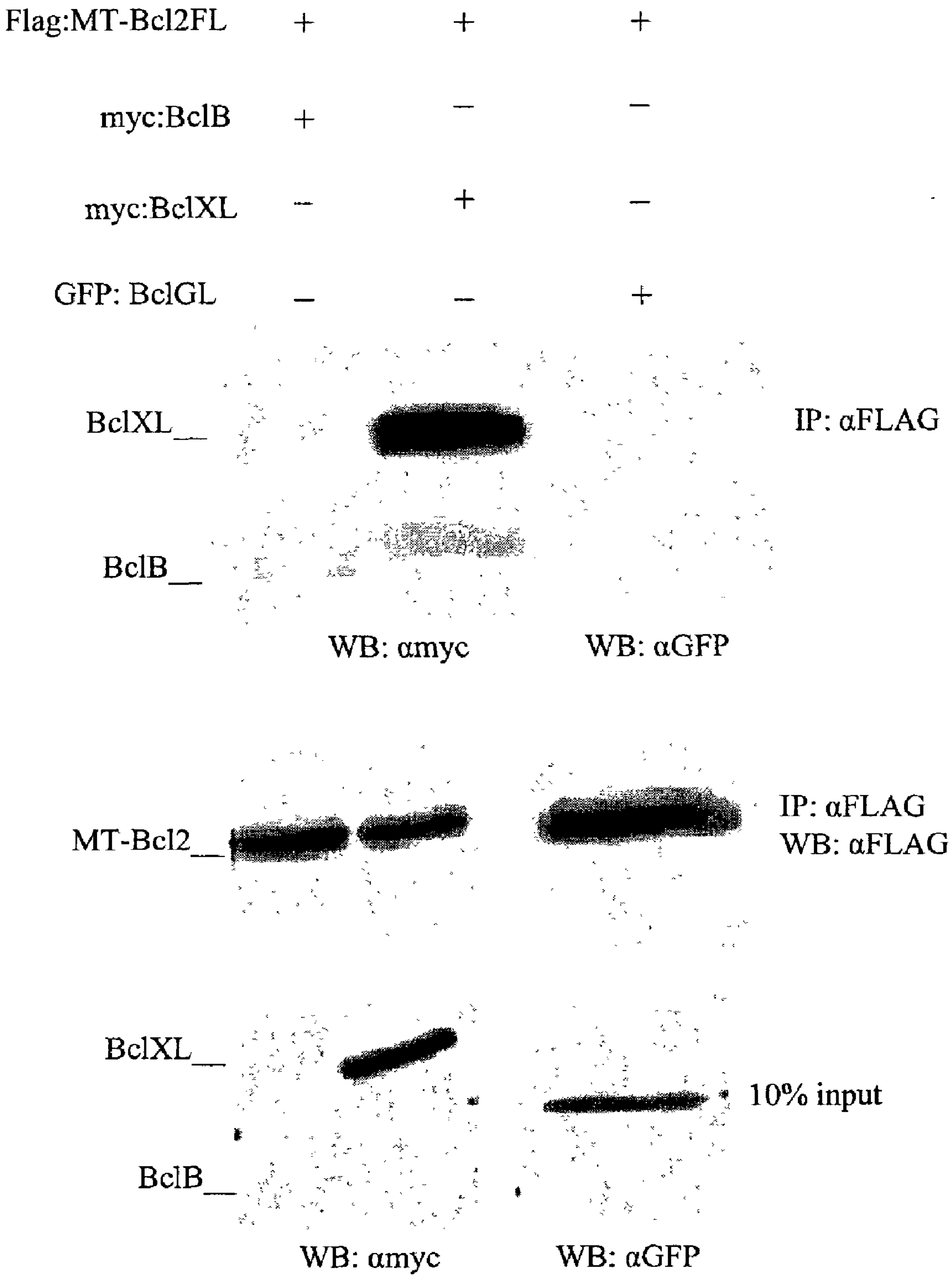
FIG. 2 shows the results of immunoprecipitating (IP) and subsequently immunoblotting (WB) HEK293T cells expressing the indicated combinations of epitope-tagged Bcl-2 family members.

HEK293T cells were cultured in DMEM supplemented with 10% FBS. Cells were then transfected using Superfect Reagent (Qiagen) with expression plasmids encoding various combinations of epitope-tagged human Bcl-2 family members (myc-BclXL, myc-BclB or GFP-BclGL) and epitope-tagged Bcl-MT (FLAG-MTBcl2-FL), as shown in FIG. 2. Transfected cells were then cultured in the presence of 50 mM benxocarbonyl-Val-ALA-Asp-fluoromethylketone (zVAD-fmk) to prevent apoptosis, and resuspended in lysis buffer (50 mM Tris-HCl, pH 7.4, 150 mM NaCl, 20 mM EDTA, 1% Nonidet P-40, 1 mM DTT, 1 mM PMSF and a protease inhibitor cocktail (Roche)). 10% of the total lysate volume was reserved. The remainder of the lysates was precleared by incubation with protein G agarose beads (Santa Cruz) for 2 hrs at 4° C. and then incubated with 10 µl of monoclonal anti-FLAG Sepharose (Covance) at 4° C. overnight. Pelleted beads were washed 4 times in lysis buffer before boiling in Laemmli sample buffer. Supernatants were subjected to SDS-polyacrylamide gel electrophoresis and immunoblotted with monoclonal anti-myc antibody (Santa Cruz) or polyclonal anti-GFP antibody (Santa Cruz).

As shown in FIG. 2, FLAG-MTBcl2-FL co-immunoprecipitated with either myc-BclXL or myc-BclB, but not with GFP-BclGL, evidencing that Bcl-MT can associate with certain mammalian Bcl-2 family members.

All journal article, reference, database and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention.

What is claimed is:

1. An isolated nucleic acid molecule consisting of the nucleotide sequence SEQ ID NO:4, or a degenerate variant thereof, wherein said nucleic acid molecule encodes the amino acid sequence of SEQ ID NO:5.

2. The isolated nucleic acid molecule of claim 1, wherein the nucleotide sequence is SEQ ID NO:4.

3. The isolated nucleic acid molecule of claim 1, operatively linked to a promoter of RNA transcription.

4. An isolated vector comprising the nucleic acid molecule of claim 1.

5. An isolated cell comprising the nucleic acid molecule of claim 1.

6. The isolated cell of claim 5, selected from the group consisting of a mammalian, a yeast and a bacterial cell.

7. The isolated cell of claim 6, wherein said cell is a mammalian cell.

8. The isolated cell of claim 6, wherein said cell is a yeast cell.

9. The isolated cell of claim 6, wherein said cell is a bacterial cell.

10. An isolated oligonucleotide consisting of at least 17 contiguous nucleotides of SEQ ID NO:4, or the full complement thereof.

11. The oligonucleotide of claim 10, labeled with a detectable marker.

12. A primer pair suitable for use in the polymerase chain reaction (PCR), comprising two oligonucleotides according to claim 10.

13. A method of producing a polypeptide comprising a Bcl-2 domain, comprising expressing the nucleic acid molecule of claim 1 in vitro or in a cell under conditions suitable for expression of said polypeptide.

* * * * *

UNITED STATES PATENT AND TRADEMARK OFFICE

CERTIFICATE OF CORRECTION

PATENT NO. : 7,588,914 B2
APPLICATION NO. : 10/294445
DATED : September 15, 2009
INVENTOR(S) : Godzik et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1113 days.

Signed and Sealed this

Twenty-first Day of September, 2010

David J. Kappos
*Director of the United States Patent and Trademark Office*